US006405577B2

(12) United States Patent
Hanashiro et al.

(10) Patent No.: US 6,405,577 B2
(45) Date of Patent: Jun. 18, 2002

(54) FLOW RATE DETECTOR MECHANISM WITH VARIABLE VENTURI AND EXHAUST GAS SAMPLING METHOD USING THE SAME

(75) Inventors: Noriyuki Hanashiro; Atsushi Shibata, both of Mie; Shigeru Yanagihara; Shuta Yamawaki, both of Tokyo, all of (JP)

(73) Assignee: Honda Giken Kogyo Kabushiki Kaisha and Kabushiki Kaisha Tsukasa Sokken, Tokyo (JP)

( * ) Notice: Subject to any disclaimer, the term of this patent is extended or adjusted under 35 U.S.C. 154(b) by 0 days.

(21) Appl. No.: 09/835,353

(22) Filed: Apr. 17, 2001

Related U.S. Application Data

(62) Division of application No. 09/349,926, filed on Jul. 8, 1999.

(30) Foreign Application Priority Data

Jul. 9, 1998 (JP) ............................................. 10-194149
Feb. 1, 1999 (JP) ............................................. 11-023422

(51) Int. Cl.[7] .............................. G01L 1/22; G01N 7/00; G01N 33/497
(52) U.S. Cl. ................ 73/23.31; 73/863.03; 73/863.11; 73/863.21; 73/863.31; 73/861.53; 73/861.63
(58) Field of Search ............................ 73/23.31, 861.52, 73/861.53, 861.55, 861.63, 863.01, 863.02, 863.03, 863.11, 863.21, 863.31

(56) References Cited

U.S. PATENT DOCUMENTS

| | | | | | |
|---|---|---|---|---|---|
| 3,603,155 A | * | 9/1971 | Morris et al. | ............... | 73/23.31 |
| 3,724,503 A | | 4/1973 | Cooke | | |
| 3,817,100 A | * | 6/1974 | Anderson et al. | ........ | 73/861.63 |
| 3,896,670 A | | 7/1975 | Converse et al. | | |
| 4,112,757 A | | 9/1978 | Hayward | | |
| 4,586,367 A | * | 5/1986 | Lewis | ....................... | 73/23.33 |
| 5,184,501 A | * | 2/1993 | Lewis et al. | ............. | 73/863.01 |
| 5,337,595 A | * | 8/1994 | Lewis | ....................... | 73/23.31 |
| 5,419,178 A | * | 5/1995 | Decker et al. | ............. | 73/23.31 |
| 5,469,731 A | * | 11/1995 | Decker et al. | ............. | 73/23.31 |
| 5,698,793 A | | 12/1997 | Carmichael | | |
| 5,846,831 A | * | 12/1998 | Silvis | ......................... | 73/23.31 |
| 5,880,378 A | | 3/1999 | Behring | | |
| 6,200,819 B1 | * | 3/2001 | Harvey et al. | ........... | 73/863.03 |

FOREIGN PATENT DOCUMENTS

| | | | | |
|---|---|---|---|---|
| JP | 54-71689 | | 6/1979 | |
| JP | 54-127388 | | 10/1979 | |
| JP | 55-65133 | | 5/1980 | |
| JP | 62-157547 | | 7/1987 | |
| JP | 4-216435 | | 8/1992 | |
| JP | 4-231868 | | 8/1992 | |
| JP | 4-268440 | * | 9/1992 | ................ 73/23.31 |
| JP | 8-226879 | * | 9/1996 | ................ 73/23.31 |

* cited by examiner

*Primary Examiner*—Daniel S. Larkin
(74) *Attorney, Agent, or Firm*—Birch, Stewart, Kolasch and Birch, LLP

(57) ABSTRACT

A flow rate detector mechanism using variable Venturi therein, comprising: a variable flow rate generator, comprising: a core 11; and a variable Venturi 12; wherein a throat (flow passage) cross-sectional area defined between the core and the venturi is able to be changed by shifting relative positions of the core and the venturi in a direction of axes thereof, and further comprising a flow rate calculation processing portion 30 for calculating a flow rate based on the relative positions in the direction of the axes thereof and for outputting the calculated flow rate, thereby continuously changing the constant flow rate, without occurrence of any disturbance therein. Further, with an exhaust gas sampling method applying the flow rate detector mechanism using variable Venturi, CVS flow rate is changed within the range of the phases of measure modes, so as to make small the difference between the peak dew point in the bag and the final dew point in the bag, as well as to causethe final dew point to approach the temperature at which the bag is kept. Therefore, the dilution ratio of the final dew point is decreased, so as to improve the accuracy in analysis.

4 Claims, 16 Drawing Sheets

FIG. 8

Sequences of Changing CVS Flow Rate and Sampling Flow Rate

| No. | Time (sec) | CVS Flow Rate (m³/min) | Sampling Flow Rate (liter/min) | No. | Time (sec) | CVS Flow Rate (m³/min) | Sampling Flow Rate (liter/min) |
|---|---|---|---|---|---|---|---|
| 1 | 117 | 1.8→1 | 9→5 | 32 | 749 | 1→0.6 | 5→3 |
| 2 | 161 | 1→2.4 | 5→12 | 33 | 764 | 0.6→1.8 | 3→9 |
| 3 | 262 | 2.4→1.8 | 12→9 | 34 | 786 | 1.8→1 | 9→5 |
| 4 | 304 | 1.8→0.6 | 9→3 | 35 | 800 | 1→1.8 | 5→9 |
| 5 | 344 | 0.6→1.8 | 3→9 | 36 | 810 | 1.8→1 | 9→5 |
| 6 | 376 | 1.8→1 | 9→5 | 37 | 818 | 1→0.6 | 5→3 |
| 7 | 390 | 1→0.6 | 5→3 | 38 | 842 | 0.6→1.8 | 3→9 |
| 8 | 399 | 0.6→1.8 | 3→9 | 39 | 853 | 1.8→1 | 9→5 |
| 9 | 419 | 1.8→0.6 | 9→3 | 40 | 948 | 1→0.6 | 5→3 |
| 10 | 444 | 0.6→2.4 | 3→12 | 41 | 959 | 0.6→1.8 | 3→9 |
| 11 | 460 | 2.4→1.8 | 12→9 | 42 | 976 | 1.8→1 | 9→5 |
| 12 | 467 | 1.8→1 | 9→5 | 43 | 1008 | 1→0.6 | 5→3 |
| 13 | 492 | 1→0.6 | 5→3 | 44 | 1052 | 0.6→1 | 3→5 |
| 14 | 510 | 0.6→1 | 3→5 | 45 | 1055 | 1→1.8 | 5→9 |
| 15 | 515 | 1→1.8 | 5→9 | 46 | 1064 | 1.8→1 | 9→5 |
| 16 | 530 | 1.8→1 | 9→5 | 47 | 1072 | 1→0.6 | 5→3 |
| 17 | 540 | 1→0.6 | 5→3 | 48 | 1103 | 0.6→1.8 | 3→9 |
| 18 | 569 | 0.6→1.8 | 3→9 | 49 | 1114 | 1.8→1 | 9→5 |
| 19 | 576 | 1.8→1 | 9→5 | 50 | 1140 | 1→0.6 | 5→3 |
| 20 | 606 | 1→1.8 | 5→9 | 51 | 1169 | 0.6→1.8 | 3→9 |
| 21 | 613 | 1.8→0.6 | 9→3 | 52 | 1179 | 1.8→0.6 | 9→3 |
| 22 | 645 | 0.6→1 | 3→5 | 53 | 1197 | 0.6→1 | 3→5 |
| 23 | 650 | 1→1.8 | 5→9 | 54 | 1234 | 1→0.6 | 5→3 |
| 24 | 661 | 1.8→1 | 9→5 | 55 | 1262 | 0.6→1 | 3→5 |
| 25 | 670 | 1→0.6 | 5→3 | 56 | 1269 | 1→1.8 | 5→9 |
| 26 | 693 | 0.6→1 | 3→5 | 57 | 1275 | 1.8→1 | 9→5 |
| 27 | 698 | 1→1.8 | 5→9 | 58 | 1303 | 1→0.6 | 5→3 |
| 28 | 711 | 1.8→1 | 9→5 | 59 | 1339 | 0.6→1 | 3→5 |
| 29 | 717 | 1→0.6 | 5→3 | 60 | 1341 | 1→1.8 | 5→9 |
| 30 | 729 | 0.6→1.8 | 3→9 | 61 | 1346 | 1.8→1 | 9→5 |
| 31 | 743 | 1.8→1 | 9→5 | 62 | 1351 | 1→0.6 | 5→3 |

101 : Orifice of 1 liter/min in Flow Rate
102 : Orifice of 2 liter/min in Flow Rate
103 : Orifice of 4 liter/min in Flow Rate
104 : Orifice of 8 liter/min in Flow Rate Problem when Changing Diluted Gas Flow Rate
by Conventional CVS

FIG. 16(B)       PRIOR ART

FLOW RATE DETECTOR MECHANISM WITH VARIABLE VENTURI AND EXHAUST GAS SAMPLING METHOD USING THE SAME

This application is a divisional of co-pending application Ser. No. 09/349,926, filed on Jul. 8, 1999, the entire contents of which are hereby incorporated by reference and for which priority is claimed under 35 U.S.C. § 120; and this application claims priority of Application No. 10-194149 and 11-023422 filed in Japan on Jul. 9, 1998 and Feb. 1, 1999, respectively under 35 U.S.C. 119.

BACKGROUND OF THE INVENTION

1. Field of the Invention

The present invention relates to a flow rate detector mechanism with a variable venturi therein for changing the value of constant flow rate with continuity, being suitable to be applied to a constant volume sampler (CVS) for diluting and sampling the exhaust gas discharged from an automobile, and further to an exhaust gas sampling method, in which the exhaust gas is diluted corresponding to the traveling mode patterns for evaluation test, using such the CVS as mentioned above wherein the variable venturi flow rate detector mechanism is applied, so as to sample the exhaust gas in a sampling bag.

2. Description of Related Art

For measuring weight of components in the exhaust gas emitted from an automobile, a sampling apparatus called a "constant volume sampler (CVS)" is used as shown, for example, in Japanese Laid-Open Patent No. Sho 54-71689 (1979) and Japanese Laid-Open Patent No. Sho 54-127388 (1979).

Further, in Japanese Laid-Open Patent No. Sho 55-65133 (1980) is described the CVS for sampling a portion of diluted gas to be analyzed, being formed at a constant flow rate, by diluting a target gas such as the exhaust gas from the automobile with fresh air, in which a constant volume pump is driven by a synchronous motor so as to form a constant flow rate of the diluted gas.

In Japanese Laid-Open Patent No. Sho 62-157547 (1987), there is described a modal mass analysis method, according to air dilution of exhaust gas from the automobile, for increasing the accuracy in analyzing the emitted amounts of components in each mode of travel, in which the flow rate of exhaust gas obtained through the air dilution method is compensated by concentration of the target components corresponding to the same phase, being obtained through interpolation. Further, in the FIG. 1 of the publication thereof is described the CVS in which the constant volume venturi and a constant volume blower are connected in series.

In Japanese Laid-Open Patent No. Hei 4-216435 (1992), there is described an exhaust gas sampling apparatus for an internal combustion engine, in particular applying the CVS (Constant Volume Sampler) method thereto for improving the accuracy and also the response in the measurement. This exhaust gas sampling apparatus for an internal combustion engine is constructed in the following manner. Within a conduit, in which flows the diluted exhaust gas being formed by mixing the exhaust gas discharged from the internal combustion engine with fresh air, is positioned a sampling conduit for sampling a portion of the diluted exhaust gas. Connected to the sampling conduit are provided a suction pump, a critical venturi, an exhaust gas analyzer, and a throttle valve, in a sequence from the downstream side of the diluted exhaust gas. Further, between the critical venturi and the exhaust gas analyzer, there is provided a passage for introducing atmospheric air into the sampling conduit. With the provision of the passage for introducing the atmospheric air into the sampling conduit, fluctuation of the pressure in an exhaust gas analyzer is suppressed to be minute or very small even when the pressure rises in the conduit in which the diluted exhaust gas flows, thereby improving the response characteristic thereof. Further, the amount of change in the pressure within the exhaust gas analyzer is small even when a large volume of the diluted exhaust gas is introduced into the conduit, thereby having no influence on the accuracy in the measurement thereof.

Further, in Japanese Laid-Open Patent No. Hei 4-216435 (1992), with provision of an flow rate integrator in an air supply conduit, there is described an exhaust gas analyzer in which a standard total passage volume at a moment can be calculated in a calculation unit by taking into consideration the pressure and temperature of gas. This exhaust gas analyzer is constructed in the following manner. A sample-taking conduit is provided, into which the mixture of the exhaust gas and fresh air is supplied through a gas intake conduit, and a gas supply pump is positioned after the gas intake conduit. The gas supply pump is constructed with a rotation pump having a constant suction capacity, for example, and a critical nozzle is positioned before the rotation pump. In the air supply conduit is provided the flow rate integrator which is constructed with a vortex flow meter (a mass flow meter based on a principle such as Karman's vortex). The output of the flow rate integrator is provided to the calculation unit. The calculation unit obtains the standard total passage volume at a moment by taking into the consideration the pressure and temperature of gas from the flow rate in the air supply conduit.

In the analysis of components in the exhaust gas with use of the CVS method in this manner, there is a necessity to alter the flow rate of the diluted gas depending upon the test modes. For example, in a cold transient (CT) phase starting from a time point when engine is started to a time point 505 seconds later, the flow rate of the diluted gas is determined to be 15 $m^3$/min, and in a cold stabilizing (CS) phase from 505 sec to 1374 sec to be 3 $m^3$/min. Further, after being stopped for ten (10) minutes from the time point at 1374 sec, the engine is re-started, and in a hot transient (HT) phase the flow rate of the diluted gas is determined to be at 3 $m^3$/min.

For altering or exchanging the flow volume of diluted gas depending upon the test modes, according to the CVS of the conventional art, a plurality of systems are provided in parallel, in each of which valves for opening and closing and a fixed venturi are connected in series, wherein the one fixed venturi of the desired flow rate is selectively used. Thus, the plurality of systems of the fixed venturis through which the diluted gas flows are switched between based on the flow rates thereof.

FIG. 16 shows problems arising when the flow rate of the diluted gas is altered in the CVS device of the conventional art. As shown in FIG. 16(a), when the flow rate of the diluted gas is altered from 15 $m^3$/min to 3 $m^3$/min by, for example, turning from a condition where the first open/close valve 102 connected to the fixed venturi 101 in series is turned OPEN thereby conducting the diluted gas at the flow rate of 15 $m^3$/min into a condition where the second open/close valve 104 of the flow rate of 3 $m^3$/min, connected to the second venturi 103 in series, is turned OPEN while turning the first open/close valve 102 CLOSED, as shown in FIG. 16(b), time delay (i.e., a region with hatching lines) occurs in the time sequence during which the flow rate of the diluted gas is altered from 15 m³/min to 3 m³/min, and disturbance in the flow rate occurs.

In the portion (in the hatched area) of the time delay in the flow rate, the flow rate of the diluted gas is larger than the desired one, i.e., 3 m³/min, however in the conventional exhaust gas analysis with use of the CVS device, since the decreased volume of the exhaust gas in the flow rate during the time delay portion (the hatched area) is not reflected upon the analysis data, an error occurs in the result of analysis of the exhaust gas components, for example, in the degree of 0.3%. Further, since the disturbance occurs after the exchange of the flow rate, it sometimes also results in decrease in accuracy of the analyzed result.

Then, with provision of a flow meter in the passage for the diluted gas for measuring the flow rate thereof continuously, it can be considered that the measured flow rate of the diluted gas is reflected in the analyzed result thereof, thereby preventing any error therein from occurring. However, the provision of the flow meter in the passage for the diluted gas not only makes the apparatus itself large in size and expensive in cost thereof, but also increases the resistance in the passage for the diluted gas. Thus, the capacity of the blower must be larger for sucking the diluted gas, and therefore this is not a wise plan or design.

Therefore, a first object of the present invention, for dissolving such the problems as mentioned above, is to provide a flow rate detector mechanism using variable venturi therein, being able to alter or exchange the flow rate with continuity by changing the cross-sectional area of a throat, so as to eliminate the disturbance occurring upon the change in the flow rate of the diluted gas, and also to enable output the flow rate data with high accuracy even when the flow rate is altered but without provision of a flow meter as described above.

Japanese Laid-Open Patent No. Sho 54-127388 (1979) discloses the following, in connection with the measurement of components of the exhaust gas.

In general, the measurement of components in the exhaust gas is practiced by measuring the concentration of the gas components in the exhaust gas that is sampled in a bag within a predetermined time period, by means of the CVS device. As a method for measuring the gas concentration of components in the exhaust gas sampled in the bag, there is known a continuous measurement method for diluted gas, by which the gas concentration of the components can be obtained as an average concentration of the gas sampled as a whole and can be measured in a moment. In this continuous measurement method for diluted gas, the gas concentration of specific component(s) in sampling gas, being sampled from the exhaust gas which is diluted with the air continuously, is measured by a continuous detector, and instantaneous weight of the gas components is calculated by computation using the measured concentration and the flow rate of the sampled gas. However, the dilution ratio comes to be one per several tens (1/several tens) depending upon the operating condition of a car (in particular, in an idling operation). In explanation, with this method, the concentration of the sample gas is decreased too much, therefore, the detector for measuring the concentrations is required to be one which has high sensitivity. Furthermore, since the concentration of the sample gas come to be low (or lean), it is impossible to measure the concentration with high accuracy, due to error and so on being caused by changes in the concentration of the target components to be measured, which are contained in the air for use in dilution thereof.

In Japanese Laid-Open Patent No. Hei 4-268440 (1992) is described an analyzer for exhaust gas of automobiles, in which the exhaust gas discharged from the engine of an automobile is diluted with a gas for dilution, at the gas being diluted at a constant rate and such that the dilution ratio provides that no dew is condensed therein, to the diluted gas then being supplied to an analyzer portion as the sampling gas.

Further, in particular in the section describing the conventional arts in Japanese Laid-Open Patent No. Hei 4-268440 (1992), it is described that, for quantitative analysis of the components contained within the exhaust gas, the exhaust gas is sampled as the sample gas with use of the CVS, during which the automobile is operated on a chassis dynamo in accordance with a driving mode, such as a 10 mode, a LA-4C/H mode, etc., to be supplied to an analyzer portion of FTIR (Fourier Transform Infrared Spectrometer).

Further, in the section describing the conventional arts in Japanese Laid-Open Patent No. Hei 4-268440 (1992), it is described that the components and the average value of concentration thereof in the diluted gas can be obtained during a certain time period, by supplying the diluted gas into an analyzer portion, which is sampled in the bags for sampling dilute gas. Further, it is also described that the result of analysis can be obtained more correctly by having measured background values in advance through analysis of the air which was sampled in the air sampling bag.

Moreover, in the description of the problems to be dissolved by the invention of Japanese Laid-Open Patent No. Hei 4-268440 (1992), it is described that since the exhaust gas is obtained through burning of organic compounds including gasoline, carbon, and hydrogen, the exhaust gas contains water vapor therein, and when the water vapor is condensed into dew, the components of the gas are reduced because they dissolve into the water condensed from the vapor. Consequently, as a means for avoiding such situations, it is described that (1) the temperature of tunnels for dilution and gas passages are maintained to be higher than a certain value, so as to prevent the exhaust from being decreased in temperature thereof, and (2) the dilution rate (multiplying factor) of the diluted gas is increased by means of the air for dilution, so as to increase the dew point.

Also, in Japanese Laid-Open Patent No. Hei 8-226879 (1996), there is described a gas sampling apparatus wherein for diluting the exhaust gas discharged from a source of exhaust gas to be sucked in by the CVS, a sampling bag device is provided in a gas sampling flow passage divided from the CVS through a suction pump and a flow rate controller device, and wherein the gas sampling flow passage is heated in the region reaching up to the sampling bags in such a degree that the moisture in gas passing therethrough is not condensed, so as to provide for measurement of components included within the exhaust gas with high accuracy, while sampling the exhaust gas being diluted at the minimum limit.

However, in the exhaust gas sampling method for analyzing the components of the diluted gas being sampled in a sampling bag, the diluted gas must be set at such a dilution ratio that no condensation of moisture occurs in the diluted gas. By increasing the flow rate of the CVS (i.e., setting the dilution ratio at a high value), it is possible to protect the diluted gas from the condensation of moisture therein. However, if the dilution ratio is increased, the influences of CO, HC, $NO_x$, and so on contained in the fresh air from outside become large, and therefore it is difficult to obtain the analysis data correctly.

Turning attention to the discharged volume of the exhaust gas in each of phases within the traveling modes, the dilution rate is decreased by making the CVS different in the flow rate thereof in each of the phases, so as to obtain the correct analysis data.

FIG. 12 and FIG. 13 are graphs showing the results of measurements in a case where the CVS flow rate is changed for each of the phases wherein, in particular, FIG. 12 shows a relationship between the flow rate of the exhaust gas in the LA-4 mode, while FIG. 13 shows the dew point in the gas sampling bag. The LA-4 mode comprises the CT phase from start of the measurement up to 505 sec, the CS phase from 505 sec up to 1,374 sec, and the HT phase starts after a 600 sec pause up to 505 sec thereafter (note that the HT phase is similar to the CT phase, and therefore is eliminated in FIGS. 8, 9, 10, 12, 13, 14, and 15). The traveling patterns, including operation states such as acceleration, constant speed, deceleration, etc. (speed patterns of automobiles), are set up corresponding to the development of time. In FIGS. 12 and 13, the traveling pattern indicates the speed (vehicle speed) of the automobile running on the chassis dynamo equipment, for testing. In FIG. 12, the flow rate of exhaust gas indicates the measured value of exhaust gas of the automobile running on the chassis dynamo equipment. The test condition shown in FIG. 12 is that the CVS flow rate in the CS phase is set at 2.4 $m^3$/min, while the CVS flow rate is set at 1.6 $m^3$/min. The sampling bags are heated at 40° C. in temperature thereof.

For such a condition, the change in the dew point within the gas sampling bag is shown in FIG. 13 in particular, using the case of a gasoline car as an example, when a portion of the exhaust gas (the diluted gas) which is diluted by means of the CVS is sampled in the gas sampling bags. In the CT phase in which the CVS flow rate is set at 2.4 $m^3$/min, the peak value of the dew point within the bag is 34.6° C. (at the dilution ratio of 3.34), however, the dew point within the bag is decreased to 32.6° C. (at the dilution ratio of 3.95) in the final stage of the CT phase. In the same manner, in the CS phase in which the CVS flow rate is set at 1.6 $m^3$/min, the peak value of the dew point within the bag is 36.0° C. (at the dilution ratio of 2.29), however, the dew point within the bags is decreased to 31.5° C. (at the dilution ratio of 4.34) in the final stage of the CS phase.

Under the condition mentioned above, since the sampling bag is heated to 40° C. in temperature thereof, no dew is condensed as long as the dew point within the sampling bag (BAG) is less than 40° C. In the measured results of the dew points within the bag shown in FIG. 13, because there still remains a margin up to 40° C., it can be considered that the diluted gas may be sampled in the sampling bag by changing the CVS flow rate down to a lesser value (i.e., by decreasing the dilution ratio), so as to sample in the sampling bag the diluted gas which is higher or richer in the exhaust gas condensation.

FIGS. 14 and 15 show the measured results of the CVS flow rates in a case where the condition is lower than those shown in FIGS. 12 and 13. In particular, FIG. 14 shows a relationship between the flow rate of exhaust gas and the CVS flow rate, and FIG. 15 shows the dew point within the sampling bag. As shown in FIG. 14, when the CVS flow rate is set at 1.84 $m^3$/min in the CT phase and the flow rate is set at 1.35 $m^3$/min in the CS phase, the peak values of the dew point within the bag come to be 38° C. in both the CT phase and the CS phase, and the final dew point within the bag to be 35.8° C. in the CT phase and 33.3° C. in the CS phase, as shown in FIG. 15, thereby enabling bringing them closer to the heating temperature of the sampling bag. However, as shown in FIG. 14, the flow rate of exhaust gas sometimes exceeds the CVS flow rate in the case where the CVS flow rate is set at 1.84 $m^3$/min in the CT phase and the flow rate at 1.35 $m^3$/min in the CS phase, and therefore it is impossible to perform the measurement correctly.

Therefore, another object according to the present invention, for dissolving such problems as mentioned above, is to provide an exhaust gas sampling method in which the diluted gas at a low dilution ratio can be sampled in the sampling bag while preventing the condensation of moisture therein, by changing the CVS flow rate corresponding to the traveling mode patterns for evaluation testing of the exhaust gas, and the diluted gas of the low dilution ratio (the diluted gas in a condition of high exhaust gas concentration) can be sampled in the sampling bag by bringing the peak value of the dew point in the bag and the final dew point in the bag towards the peripheral temperature of the bags, thereby increasing the accuracy in analysis of the exhaust gas components.

SUMMARY OF THE INVENTION

According to the present invention, for achieving the first object of the invention mentioned above, there is provided a flow rate detector mechanism using variable venturi therein, comprising:

a variable flow rate generator, comprising:

a core; and a variable critical flow venturi;

wherein a throat cross-sectional area defined between the core and the variable critical flow venturi may be changed by shifting relative positions of the core and the variable critical flow venturi in a direction of axes thereof;

the flow rate detector mechanism further comprising a flow rate calculation processing portion for calculating a flow rate on basis of the relative positions in the direction of the axes thereof and for outputting the calculated flow rate.

With the flow rate detector mechanism using variable venturi therein, since it is possible to change the value of constant flow rate continuously, no disturbance occurs in the value thereof when the flow rate is altered. Further, with the flow rate detector mechanism using variable venturi therein, according to the present invention, it is possible to output the flow rate value even when the flow rate is altered. Accordingly, upon analyzing the exhaust gas components, it is possible to reflect the change in the flow rate, occurring when the flow rate is altered, in the analysis data, thereby outputting the result of analyzing correctly. Accordingly, with using the flow rate detector mechanism using variable venturi therein, according to the present invention, no error is contained in the result of analysis even when the flow rate of the diluted gas is altered corresponding to the test modes, thereby the results of analysis may be obtained with high accuracy.

Next, according to the present invention, for achieving the second object mentioned above, there is provided an exhaust gas sampling method for analyzing exhaust gas of an automobile, using a flow rate detector mechanism using variable venturi therein, comprising the following steps:

diluting the exhaust gas from the automobile with fresh air from outside;

sampling a portion of the diluted exhaust gas into a sampling bag at a certain ratio; and analyzing the diluted exhaust gas being sampled, wherein a flow rate through said flow rate detector mechanism is changed in a phase of mode for measurement, so that at least a final dew point in the sampling bag approaches a predetermined temperature within a predetermined temperature range.

Further, according to the present invention, it is preferable that the flow rate through said flow rate detector mechanism is changed in the phase of mode for measurement, so that the dew point in the sampling bag is averaged. Also, the flow rate through said flow rate detector mechanism is changed in the phase of mode for measurement, so that at least the flow rate through said flow rate detector mechanism does not exceed the flow rate of the exhaust gas during the measurement. Furthermore, it is preferable to change the flow rate of the sampling gas depending upon a change in the flow rate through said flow rate detector mechanism.

Applying the exhaust gas sampling method according to the present invention, it is possible to make small the difference between the peak value in the dew point within the bag and the final dew point within the bag, as well as to cause the final dew point to approach the temperature at which the bag is maintained. Accordingly, it is possible to lower the dilution ratio at the final dew point within the bag, as well as to improve the accuracy of the analysis.

BRIEF DESCRIPTION OF THE DRAWINGS

FIG. 8 is an explanatory view of a sequence for changing diluted gas flow rate in the LA-4 mode;

DETAILED DESCRIPTION OF THE PREFERRED EMBODIMENTS

Figure 1:
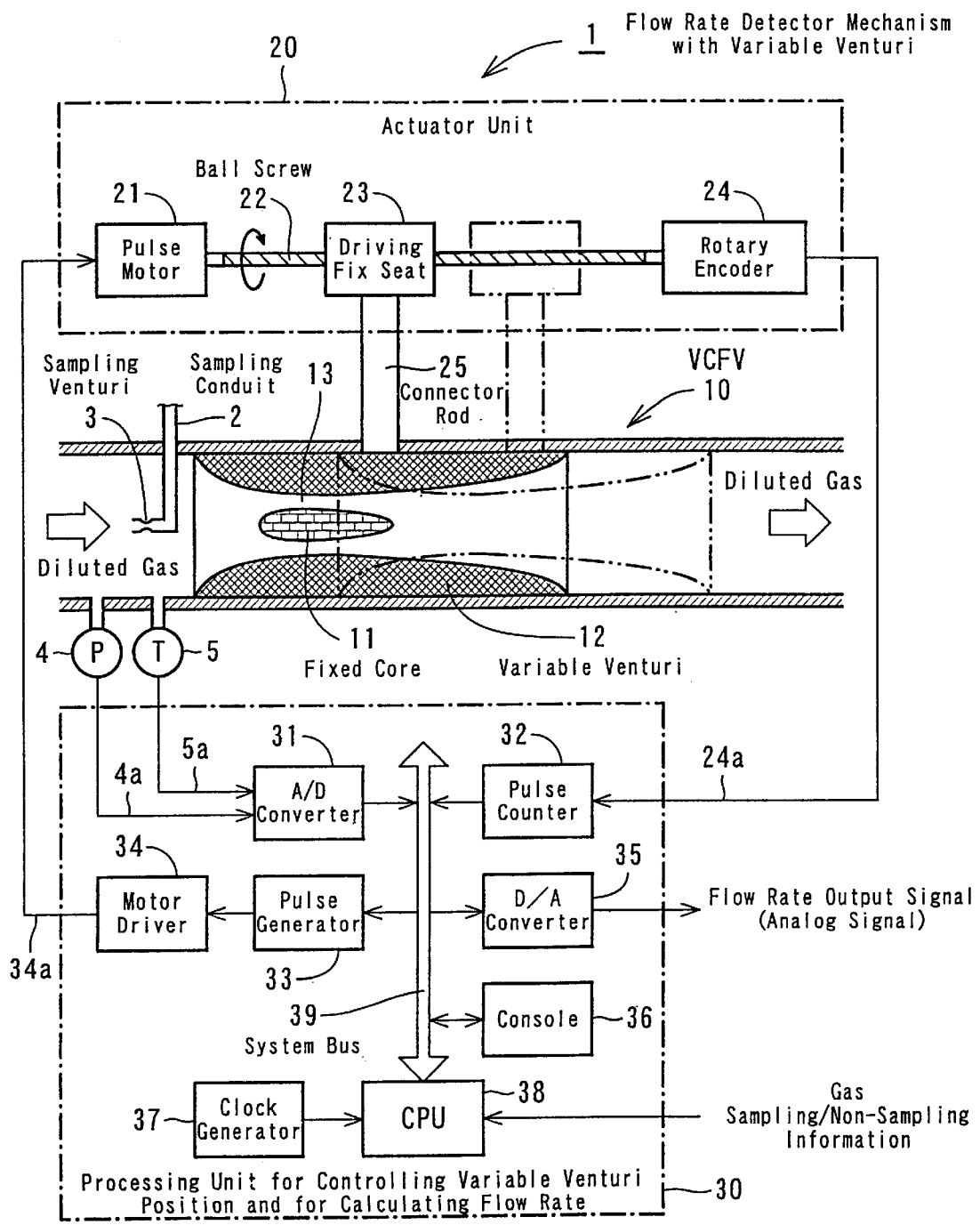
FIG. 1 is a structural view of a flow rate detector mechanism using a variable venturi therein according to the present invention.

Hereinafter, detailed explanation of the embodiments according to the present invention will be given by referring to the attached drawings. FIG. 1 shows the construction of a flow rate detector mechanism with a variable venturi according to the present invention, wherein the flow rate detector mechanism 1 with the variable venturi comprises a VCFV (Variable Critical Flow Venturi) 10 which can change the value of constant (critical) flow with continuity, an actuator unit 20, and a processing unit 30 for controlling the position of the variable venturi and for calculating the flow rate.

As the variable critical flow venturi (VCFV) is used the so-called sonic-type venturi. This variable critical flow venturi (VCFV) comprises a fixed core 11 and a variable (or movable) venturi 12. The fixed core 11 is fixed at a central position of a venturi conduit. The variable venturi 12 is so constructed that it can be shifted in an axial direction of the venturi conduit. The cross-sectional area (the cross sectional area of the flow passage) of a throat (flow passage) portion 13 between the fixed core 11 and the variable venturi 12 is changed continuously by shifting the variable venturi 12 in the axial direction thereof, thereby obtaining the construction for changing the value of flow rate continuously.

Though in FIG. 1 is shown a construction wherein the core is fixed while the venturi at an outside thereof can be shifted, it may however also be constructed so that the venturi at an outside is fixed while the core can be shifted.

At an inflow side of the variable critical flow venturi (VCFV) 10 is connected a sampling conduit 2 for sampling the sample gas. At the tip of the sampling conduit 2 is provided a sampling venturi 3 for the purpose of maintaining the sampling flow rate at a predetermined flow rate. Further, at the inflow side of the variable critical flow venturi (VCFV) 10, there are provided a pressure sensor 4 for detecting the pressure of the diluted gas as well as a temperature sensor 5 for detecting the temperature of the diluted gas, respectively.

An actuator unit 20 comprises a pulse motor 21, a ball screw 22 which is rotated upon the rotation of an output shaft of the pulse motor 21, a driving fix seat 23 which can be shifted in the direction of the axis of the ball screw 22 following the rotation thereof, and a rotary encoder 24 which detects the rotation angle of the ball screw 22 and outputs pulse signals for plural systems responding to each predetermined rotation angle of the ball screw 22.

The fix sheet 23 and the variable venturi 12 at the side of the VCFV 10 are connected to each other through a connector rod 25. Therefore, the variable venturi 12 is shifted following the shift of the driving fix seat 23 in the axial direction thereof, when the ball screw 22 is rotated by driving the pulse motor 21. Thereby, it is possible to vary the value of flow rate of the variable critical flow venturi (VCFV) 10 continuously.

A processing unit 30 for controlling the position of the variable Venturi and for calculating the flow rate comprises an A/D converter 31, a pulse counter unit 32, a pulse generating unit 33, a motor driver unit 34, a D/A converter unit 35, a console unit 36, a clock generating unit 37, a CUP unit 38, and a system bus 39. The A/D converter 31, the pulse counter unit 32, the pulse generating unit 33, the D/A converter unit 35, and the console unit 36 are connected to the CUP unit 38 through the system bus 39 being, for example, an address/data/control bus.

An output signal 4a of the pressure sensor 4 (the pressure at the inflow portion of the variable venturi) and an output signal 5a of the temperature sensor 5 (the temperature at the inflow portion of the variable venturi) are provided to the A/D converter 31 having a multiple type A/D converter therein, respectively. The A/D converter 31 converts the voltage signals into digital data corresponding to the pressure and the temperature, so as to output them as such. The digital data relating to the pressure and the temperature are provided to the CPU unit 38 through the system bus 39.

An output signal 24a of the rotary encoder 24 (pulse signal corresponding to the shift distance of the variable venturi) is provided to the pulse counter unit 32. The pulse counter unit 32 decides the direction in shifting of the variable venturi 12 on the basis of the output signal 24a of the rotary encoder 24, and also calculates the data of shift distance (position) of the variable venturi 12 on the basis of the result of counting the number of pulses so as to output the data of shift distance (position) being calculated therewith. The data of shifting distance (position) is also provided to the CPU unit 38 through the system bus 39.

The pulse generating unit 33 produces a motor driving pulse signal corresponding to the direction in rotation of the pulse motor, being designated on the basis of a pulse motor driving command when the pulse motor driving command is provided from the CPU unit 38 through the system bus 39, so as to provide the motor driving unit 34 with the motor driving pulse signal being generated.

The D/A converter unit 35 produces a voltage signal (flow rate output signal) corresponding to the flow rate on the basis of the data of flow rate which is provided from the CPU unit 38 through the system bus 39 to be outputted therefrom. Although there is disclosed the structure wherein the voltage signal (analog signal) is outputted as the flow rate output signal corresponding to the flow rate outputted in the present embodiment, it can, however, be so constructed that the data of flow rate output (the value of flow rate) is directly outputted therefrom. Also, it can be structured so that not only the flow rate (instantaneous flow rate), but also an integrated value of the flow rate, which is integrally calculated with the CPU unit 38, may be outputted.

The console unit 36 comprises an input operating portion for inputting information such as the flow rate, a condition for changing the flow rate and parameter(s) for calculating the flow rate, and a display portion on which are indicated the flow rate and the condition for changing the flow rate which are determined, as well as the present value of flow rate (instantaneous flow rate) and the integrated value of flow rate, etc.

The clock generating unit 37 provides a system clock as the basis for operation of the CPU unit 38. Also, the clock generating unit 37 provides the CPU unit 38 with a signal of a predetermined period (for example, 10 msec in the period) which is obtained by dividing the system clock output as, for example, an interruption signal for initiating the calculation of flow rate.

Figure 2:
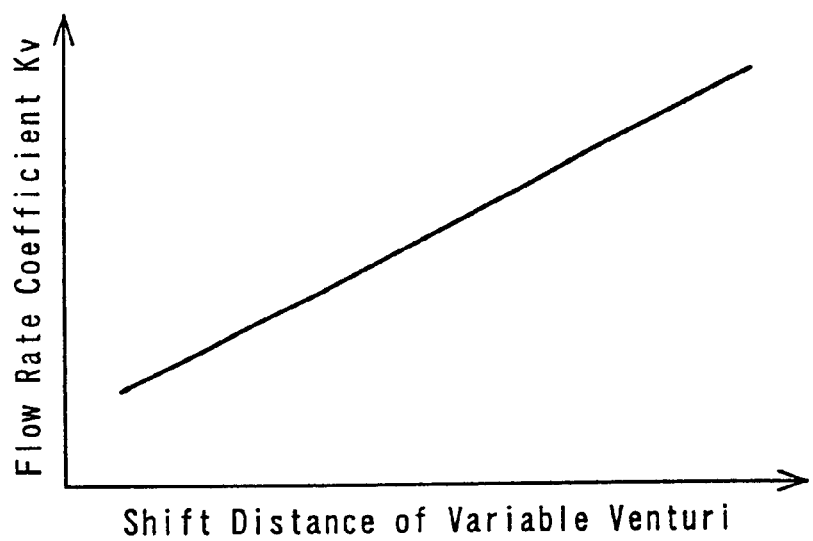
FIG. 2 is a graph showing a relationship between shift distance (position) of the variable venturi and flow rate coefficient.

The CPU unit 38 comprises a table indicating correspondence between the shift distance (position) of the variable venturi 12 and flow rate coefficient Kv of the variable critical flow venturi (VCFV) 10. FIG. 2 shows one example of a relationship between the shift distance (position) of the variable venturi and the flow rate coefficient Kv. In the present embodiment, the fixed core 11 and the variable venturi 12 are configured in the shapes thereof so that the shift distance (position) of the variable venturi is proportional to the flow rate coefficient Kv.

However, rather than providing the correspondence table which was prepared in the CPU unit 38 in advance, it also can be so structured that an equation is provided therein, through which the flow rate coefficient Kv of the variable critical flow venturi (VCFV) 10 is obtained on the basis of the shift amount (position) of the variable venturi 12. Further, regarding the data of the correspondence table and the equation, they can be inputted and/or altered through the console unit 36.

Figure 3:
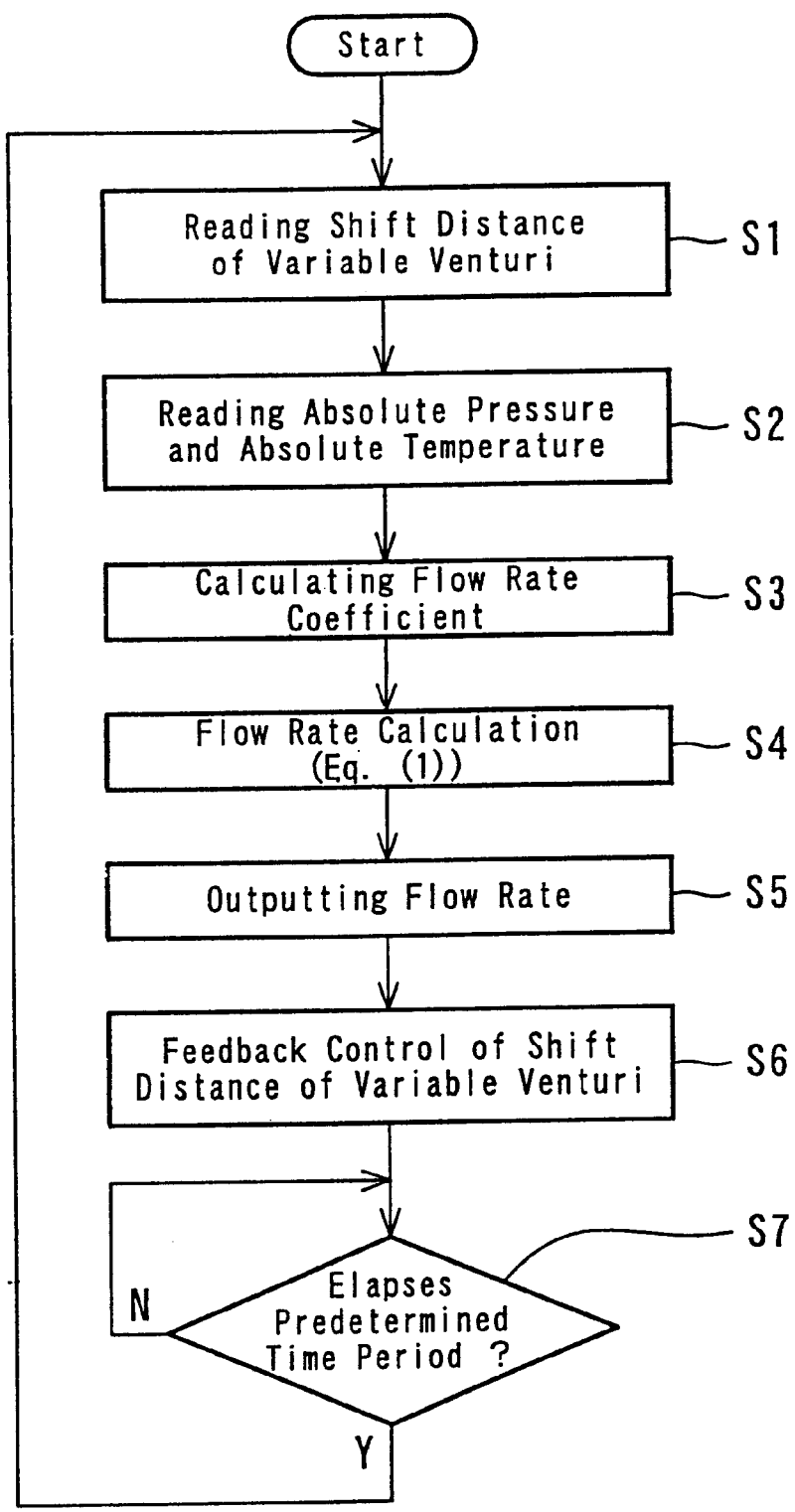
FIG. 3 is a flow chart showing processing in a CPU unit.

FIG. 3 is a flow chart showing processing in the CPU unit. The CPU unit 38, by repeating a series of steps shown in FIG. 3 at every cycle of the predetermined period (for example, a period of 10 msec.), performs the calculation of the flow rate, as well as the calculation of integration of the flow rate. Also, the CPU unit 38 controls the position of the variable venturi 12, so as to obtain the flow rate which is set through the console unit 36, through a feedback control, and controls that position of the variable venturi 12 so as to alter it when the set up flow rate is altered.

Namely, the CPU unit 38 reads the shift distance (position) of the variable venturi 12 through the pulse counter unit 32 therein (step S1). Next, the CPU unit 38 reads the absolute pressure P at the inlet of the variable critical flow venturi (VCFV) 10 and the absolute temperature at the inlet thereof through the A/D converter unit 31 (step S2). The CPU unit 38 obtains the flow rate coefficient Kv at the present shift distance (position) of the variable venturi 12, by referring to the correspondence table between the shift distance of the variable venturi 12 and the flow rate coefficient of the variable critical flow venturi (VCFV) 10 (step S3).The CPU unit 38 obtains the flow rate Q of the variable critical flow venturi (VCFV) 10 on the basis of the flow rate coefficient Kv, the inlet absolute pressure P and the inlet absolute temperature of the variable critical flow venturi (VCFV) 10, by conducting the calculation indicated by the following equation (1) (step S4).

$$Q = (Kv + Kvs) \times \frac{P}{\sqrt{T}} \qquad \text{(Eq. 1)}$$

where, Q: instantaneous flow rate of VCFV [m$^3$/min], Kv: flow rate coefficient of VCFV, Kvs: flow rate coefficient of sampling venturi, P: inlet absolute pressure of VCFV [kPa], and T: inlet absolute temperature of VCFV [K].

The CPU unit 38 displays the flow rate Q obtained in the step S4 on the display portion of the console unit 36 for the flow volume, as well as providing the flow rate output signal to an external equipment (for example, a controller device 90 shown in FIG. 5) through the D/A converter unit 35. Further, the CPU unit 38 conducts the integration of the flow rate on the basis of the flow rate Q so as to display the integrated flow rate on the display portion of the console 36 for the integrated flow rate (step S5). However, the CPU unit 38 can be so constructed that it outputs the integrated flow rate to the external equipment (such as the controller device 90 shown in FIG. 5).

Figure 5:
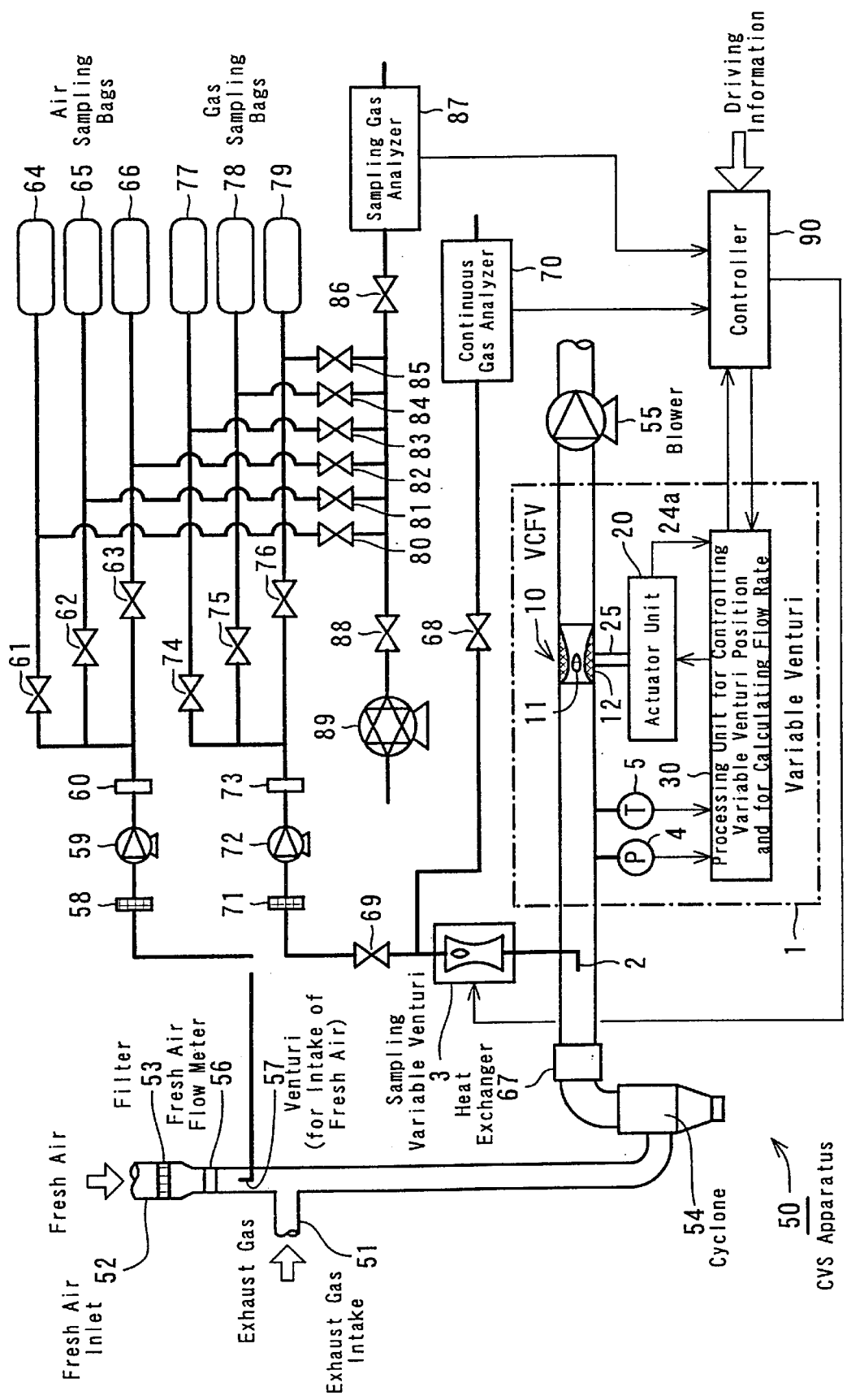
FIG. 5 is a structural view of a constant volume sampler (CVS) applying the flow rate detector mechanism with variable venturi therein, according to the present invention.

The CPU unit 38 obtains the deviation of the flow rate Q obtained in step S4 from a target flow rate (for example, a CVS flow rate which is designated with the controller device 90 shown in FIG. 5), and drives the actuator unit 20 through the pulse generator unit 33 and the motor driver unit 34 in such a direction that the deviation approaches zero (0) when the deviation is formed to exceed a permissible value which is determined in advance. Thereby, the feedback control of the shift distance (position) of the variable venturi can be performed (step S6).

As shown in step S7, the CPU unit 38 repeats the above steps S1 through S6 every time when the predetermined time period elapses. Assuming that the repetitive time period (the predetermined time period) of those steps is 10 msec, for example, the calculation of the flow rate and the feedback control of the shift distance of the variable venturi are performed every 10 msec. In the present embodiment, the series of processing of those steps is conducted upon the interruption signal supplied from the clock generating unit 37. Note that rather than supplying the interruption signal from outside, the elapse of the predetermined time period can be decided using an internal timer or the like within the CPU unit 38. Further, though the example is shown wherein the flow rate is outputted in step S5 after conducting the flow rate calculation shown in step S4, as in FIG. 3, the processing of steps S1 through S4 can, however, also be conducted to calculate out the flow rate after outputting the flow rate being obtained previously, at the time point when the predetermined time elapses. With outputting the flow rate output at the beginning of the series of steps, it is possible to correctly synchronize the timing of outputting the flow rate with the predetermined period.

In the present embodiment, as shown by the equation (i.e., Eq. (1)) for calculating the flow rate, obtaining a sum of the flow rate coefficient of the variable critical flow venturi (VCFV) 10 (the flow amount coefficient obtained corresponding to the shift distance (position) of the variable venturi) and the flow rate coefficient of the sampling venturi 3, the instantaneous flow rate Q is obtained from it taking the temperature T and the pressure P into the consideration. Accordingly, even in the condition where the sampling gas is sampled through the sampling venturi 3, it is possible to obtain a total flow rate, adding the flow rates of sampling gas. However, when no sampling gas is sampled from the sampling venturi 3, as shown in FIG. 1, information indicative of non-sampling of the sampling gas (gas sampling/non-sampling information) is provided to the CPU unit 38. The CPU unit 38, when acknowledging the gas non-sampling condition on the basis of the gas sampling/non-sampling information, turns the flow rate coefficient of the sampling venturi 3 to zero (0) and conducts the calculation of the instantaneous flow rate Q using only the flow rate coefficient of the variable critical flow venturi (VCFV) 10.

With the construction mentioned above of the flow rate detector mechanism 1 with the variable venturi shown in FIG. 1, it is possible to change or alter the flow rate of the diluted gas or the like, on the basis of the flow rate or the flow rate changing program set up in advance. Also, it is possible to calculate the instantaneous flow rate so as to display it on the display portion of the console unit 36, as well as to provide it to external equipment (such as the controller device 90 shown in FIG. 5). With the construction wherein the ball screw 22 is driven by the pulse motor 21 so as to shift the position of the variable venturi 12, it is possible to control the shift distance (position) of the variable venturi 12 within the accuracy of 10 μm, for example. Therefore, it is possible to control the flow rate correctly, as well as to alter or change the flow rate continuously without a disturbance in the flow rate value occurring even when the flow rate is changed.

However, in order to alter or change the flow rate quickly, when changing the phase under which it is measured, it can be controlled in the following manner ((1) through (4)):

(1) When the established flow rate is changed first in FIG. 1, the change of flow rate is sent by the console unit 36 to the CPU unit 38.

(2) In the console unit 36, the pulse motor 21 is driven to move the variable venturi 12 by the shift distance (position) thereof depending upon the flow rate, according to "the flow rate and the shift distance (position) of the variable venturi 12" (in the proportional relationship) which was set up in advance, through the pulse generator unit 33 and the motor driver unit 34.

(3) The driving fix seat 23, which is moved by the pulse motor, is monitored as for whether it shifts out of the predetermined position or not, by means of the rotary encoder 24, the pulse counter unit 32, and the CPU unit 38, and an alarm is generated when it shifts out of the predetermined position.

(4) At the same time of the above (1) to (3), the flow rate Q is obtained periodically (for example, at the time period of 10 msec) from the value Kv, which can be obtained from the values of the pressure sensor 4 and the temperature sensor 5, and the shift distance of the variable venturi 12.

Figure 4:
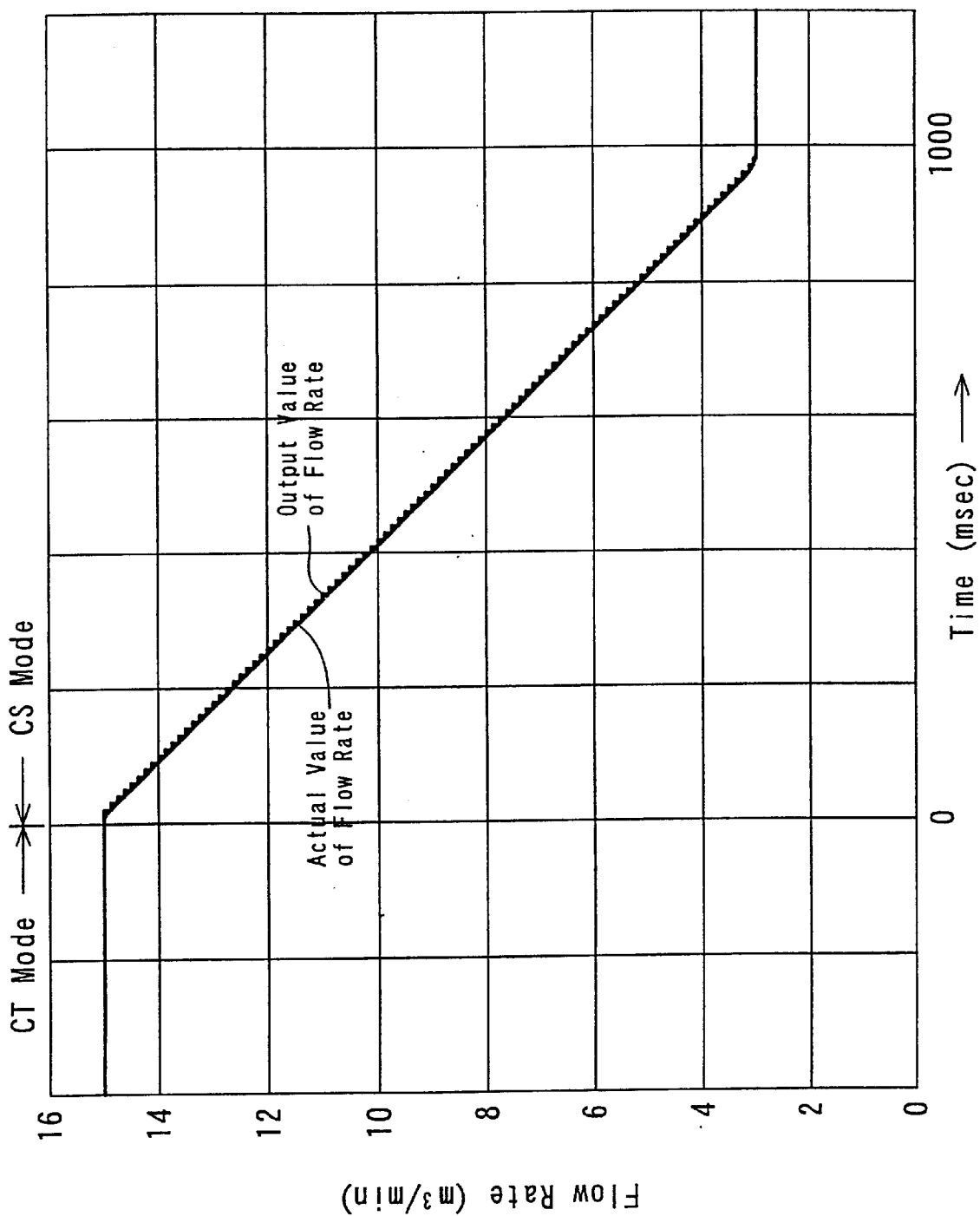
FIG. 4 is a graph showing an output characteristic of flow rate when the flow rate is changed.

FIG. 4 is a graph showing an output characteristic of flow rate when altering or exchanging the flow rate. In FIG. 4, modeled on the manner of changing from the cold transient (CT) phase (for example, at flow rate of 15 m³/min) to the cold stabilize (CS) phase (for example, at flow rate of 3 m³/min), there is shown an example of the output of flow rate in a case where it is changed within the time period of about 1 sec. With the flow rate detector mechanism 1 using a variable venturi therein, since it calculates to output the flow rate in the period (for example, 10 msec) being sufficiently shorter than the time necessary for change of the flow rate, it is possible to determine a degree in change of the flow rate correctly, and there is no large error contained in the integrated value of flow rate with integrating the instantaneous flow rate Q which is outputted at the period being sufficiently short (for example, 10 msec), thereby obtaining the integrated value of flow rate with high accuracy is possible.

FIG. 5 is a view showing the structure of the constant volume sampler (CVS) using the flow rate detector mechanism with the variable venturi mentioned above, according to the present invention. The constant volume sampler (CVS) 50 shown in FIG. 5 is able to analyze the components in the exhaust gas simultaneously (in real-time), continuously analyzing the components of the diluted gas which is obtained by mixing the exhaust gas and external fresh air together, or to analyze the components of the diluted gas which is sampled after being sampled in the sampling bag.

The exhaust gas, from the automobile installed on a chassis dynamo not shown in the figure, is supplied to an intake 51 for exhaust gas through a flexible pipe and so on, which are not shown in the figure. The exhaust gas is mixed with the external fresh air, which is taken from an air intake 52 and is purified through a filter unit 53, so as to form the diluted gas, and this diluted gas is supplied to the variable critical flow venturi (VCFV) 10, after being removed and divided from dust and mist contained therein through a cyclone unit 54. In a later stage of the variable critical flow venturi (VCFV) 10 is connected a blower 55 of a constant capacity. The constant capacity blower 55 being used here has an emitting capacity being sufficiently larger than the maximum value of flow rate of the variable critical flow venturi (VCFV) 10. Through using the constant capacity blower 55 having such a large emitting capacity, the flow rate of the diluted gas can be preset through the variable critical flow venturi (VCFV) 10. The diluted gas emitted from the constant capacity blower 55 is discharged into the air, or is discharged through a purifying apparatus not shown in the figure and then into the air.

In a side upstream from the exhaust gas intake 51, there is provided an air flow detector 56 for detecting the flow rate of the external fresh air and a venturi 57 for sampling the fresh air sample. The output of the detected flow rate of the air flow detector 56 (not shown in the figure) is provided to the controller 90. The fresh air sampled through the venturi 57 for sampling the fresh air sample is supplied through a filter unit 58 to a pump 59 for sampling the fresh air. The filter unit 58 is provided for preventing suction of foreign materials into the pump 59. An output of the pump 59 is supplied through a flow rate detector 60 for the sampled fresh air to one end of each of the respective electromagnetic valves 61, 62, and 63. The other ends of the electromagnetic valves 61, 62, and 63 are connected to the air sampling bags (sampling bags) 64, 65, and 66, respectively. There is used the pump 59 having a capacity being larger than the flow rate of the fresh air sampling venturi 57.

Accordingly, by turning the first electromagnetic valve 61 OPEN under the condition of driving the fresh air sampling pump 59, it is possible to sample the fresh air into the first air sampling bag 64. In the same manner, by turning the second electromagnetic valve 62 OPEN, the fresh air can be sampled into the second air sampling bag 65, and by turning the third electromagnetic valve 63 OPEN, into the third air sampling bag 66. An output of the detected flow rate (not shown in the figure) from the flow rate detector 60 for the sampled fresh air is provided to the controller 90. The controller 90 adjusts the volume of sampling the fresh air into the air sampling bag, by integrating the flow rate on the basis of the output of the detected flow rate from the flow rate detector 60. Also, the controller 90 performs the selection of the air sampling bags as well as the adjustment of the sampling volume thereof, by controlling OPEN/CLOSE of the electromagnetic valves 61 to 63, via signal lines for controlling the electromagnetic valves which are not shown in the figure.

It is also possible to provide a heat exchanger 67 in the upper stream side of the variable critical flow venturi (VCFV) 10, so as to heat or cool the diluted gas, thereby keeping the temperature thereof within a predetermined temperature range. With the control of temperature of the diluted gas, it is possible to prevent the condensation of moisture therein. Further, relief from fluctuation in temperature of the diluted gas makes the flow rate control stable, thereby improving the accuracy of measurement.

The diluted gas, which is sampled through the sampling Venturi 3 provided at the inlet side of the variable critical flow venturi (VCFV) 10, is supplied to one end of an electromagnetic valve 68 for continuous gas analysis, and further to one end of an electromagnetic valve 69 for sampling the diluted gas. When the electromagnetic valve 68 for continuous gas analysis is controlled to be OPEN, the diluted gas being sampled through the sampling venturi 3 is supplied to an analyzer 70 for continuous gas analysis. Thereby, the analysis of gas is conducted continuously.

When the electromagnetic valve 69 for sampling the diluted gas is controlled to be OPEN, the diluted gas sampled through the sampling venturi 3 is supplied through a filter 71 to a pump 72 for sampling the diluted gas. An output of the pump 72 is supplied through a flow rate detector 73 of the diluted gas to one end of each of respective electromagnetic valves 74, 75, and 76. The other ends of the electromagnetic valves 74, 75, and 76 are connected to sampling bags for the diluted gas 77, 78, and 79, respectively. The pump 73 having a capacity being larger than the flow rate of the sampling venturi 3 is utilized.

Accordingly, under the condition where the electromagnetic valve 69 for sampling the diluted gas is OPEN and the pump 72 for the sampling is driven, the diluted gas can be sampled in the first sampling bag 77 by turning the first electromagnetic valve 74 to OPEN. In the same manner, the diluted gas can be sampled in the second sampling bag 78 by turning the second electromagnetic valve 75 to OPEN, and in the third sampling bag 79 by turning the third electromagnetic valve 76 to OPEN. An output of the detected flow rate (not shown in the figure) from the flow rate detector 73 for the diluted gas is provided to the controller 90. The controller 90 adjusts the volume of sampling the sample gas into the sampling bag, by integrating the flow rate on the basis of the output of the detected flow rate from the flow rate detector 73 for the diluted gas. Also, the controller 90 performs the selection of the sampling bags as well as the adjustment of the sampling volume thereof, by controlling OPEN/CLOSE of the electromagnetic valves 74 to 76, via signal lines for controlling the electromagnetic valves which are not shown in the figure.

By turning to OPEN an electromagnetic valve 80 and an electromagnetic valve 86 for analyzing the sampled gas, the fresh air sampled in the first air sampling bag 64 is supplied to an analyzer 87 of the sampled gas, so as to analyze the components of the fresh air which is sampled in the first air sampling bag 64. However, the analyzer 87 for the sampled gas comprises a pump (not shown in the figure), thereby sucking the fresh air or the sample gas (the diluted gas) into the bag to supply it to the analyzing portion of components (not shown in the figure). The fresh air or the sample gas (the diluted gas), being completed in component analysis thereof, is discharged into the air, or is discharged through the purifying apparatus not shown in the figure then into the air.

In the same manner, the fresh air sampled in the second air sampling bag 65 can be supplied to the analyzer 87 of the sampling gas by turning the electromagnetic valve 81 and the electromagnetic valve 86 for analysis of the sampling gas to OPEN, and the fresh air sampled in the third air sampling bag 66 can be supplied to the analyzer 87 of the sampled gas by turning the electromagnetic valve 82 and the electromagnetic valve 86 for analysis of the sampled gas to OPEN. Further, the diluted gas (the sampling gas) sampled in the first sampling bag 77 can be supplied to the analyzer 87 for the sampled gas, by turning the electromagnetic valve 83 and the electromagnetic valve 86 for analysis of the sampled gas to OPEN. In the same manner, the sampling gas (the diluted gas) sampled in the second sampling bag 78, by turning the electromagnetic valve 84 and the electromagnetic valve 86 for analysis of the sampled gas into OPEN condition, or the diluted gas (the sampling gas) sampled in the third sampling bag 79, by turning the electromagnetic valve 85 and the electromagnetic valve 86 for analysis of the sampled gas into OPEN condition, can be supplied to the analyzer 87.

In the present embodiment, the circumference temperature around each of the diluted gas sampling bags (sampling bags) 77 to 79 is maintained at 40° C., by heating with a heater not shown in the figure, or by positioning it within a thermostatic chamber not shown in the figure.

Also, the inside of the first air sampling bag 64 can be cleaned by repeating the process of supplying the cleaning air or cleaning gas into the first air sampling bag 64 by operating a reversible pump 89 under the condition that an electromagnetic valve 88 for cleaning bag as well as the electromagnetic valve 80 are OPEN, then discharging to the outside the cleaning air or the cleaning gas therein. Cleaning each of the bags 64 to 66 and 77 to 79 can be conducted by treating each respectively by the same process.

The controller 90 provided for controlling total operation of the CVS 50 is constructed with a computer system. The controller 90 controls the OPEN/CLOSE condition of each electromagnetic valve, each of the pumps, and the blower, etc. through an output interface unit not shown in the figure. Also, the controller 90 provides the data relating to the values of flow rates, which are produced by the variable critical flow venturi (VCFV) 10, to the detector 1 with the variable venturi, so as to control the value of the constant flow rate of the diluted gas. Further, the controller 90 also can be so constructed that operating conditions (start/stop of engine, revolution number of engine, etc.) of the engine for the automobile is controlled therewith, i.e., a target to be measured in the exhaust gas therefrom. In this instance, the controller 90 controls the operation conditions in the engine of the automobile, which is installed on the chassis dynamo not shown in the figure, on the basis of operation information supplied from an automatic engine operation controller not shown in the figure, i.e., the controller 90 acknowledges the traveling mode of the automobile. Then, the controller 90 alters the flow rate through the variable venturi 1 (i.e., control of flow rate of the diluted gas) depending upon the traveling mode of the automobile, and also alters the flow rate of the variable venturi 3 for sampling in synchronism with the change in flow rate of the variable venturi 1 (i.e., control in sampling flow rate).

Further, the controller 90 obtains the flow rate of the exhaust gas discharged from the automobile by subtracting the flow rate of the external fresh air, detected by the air flow rate detector 56, from the instantaneous flow rate Q which is outputted from the flow rate detector mechanism 1 using the variable venturi therein. Under the condition of analyzing the gas continuously, the controller 90 calculates the concentration of the exhaust gas and the weight of each component thereof on the basis the analysis data for each component outputted from the continuous gas analyzer 70 and the flow rate of the exhaust gas discharged from the automobile, so as to display the calculated results (analysis results) on a screen of an image display apparatus not shown in the figure, or to print it out via a printer not shown in the figure. Moreover, the controller 90 can provide the calculated results (analysis results) to equipment of a higher rank. Also, the controller 90 can obtain the concentration of the exhaust gas and the weight of each component thereof with compensation of the contents of the fresh air for use in dilution, when the analysis of the sampled gas is completed so that the components of the dilution air are known. In the analyzing mode for the sampling gas, the controller 90 conducts the analysis of the sampling gas through the sampling gas analyzer 87, so as to output the concentration of the exhaust gas and the weight of each component thereof with compensation for the contents of the fresh air.

The CVS 50 shown in FIG. 5 can control the flow rate with high accuracy since it can alter or exchange the flow rate continuously and also uses the flow rate detector mechanism 1 with the variable venturi, with which the instantaneous flow rate can be obtained correctly. At the same time, since no disturbance occurs during changing of the flow rate thereof, the CVS 50 enables the measurement of the exhaust gas with high accuracy.

Figure 6:
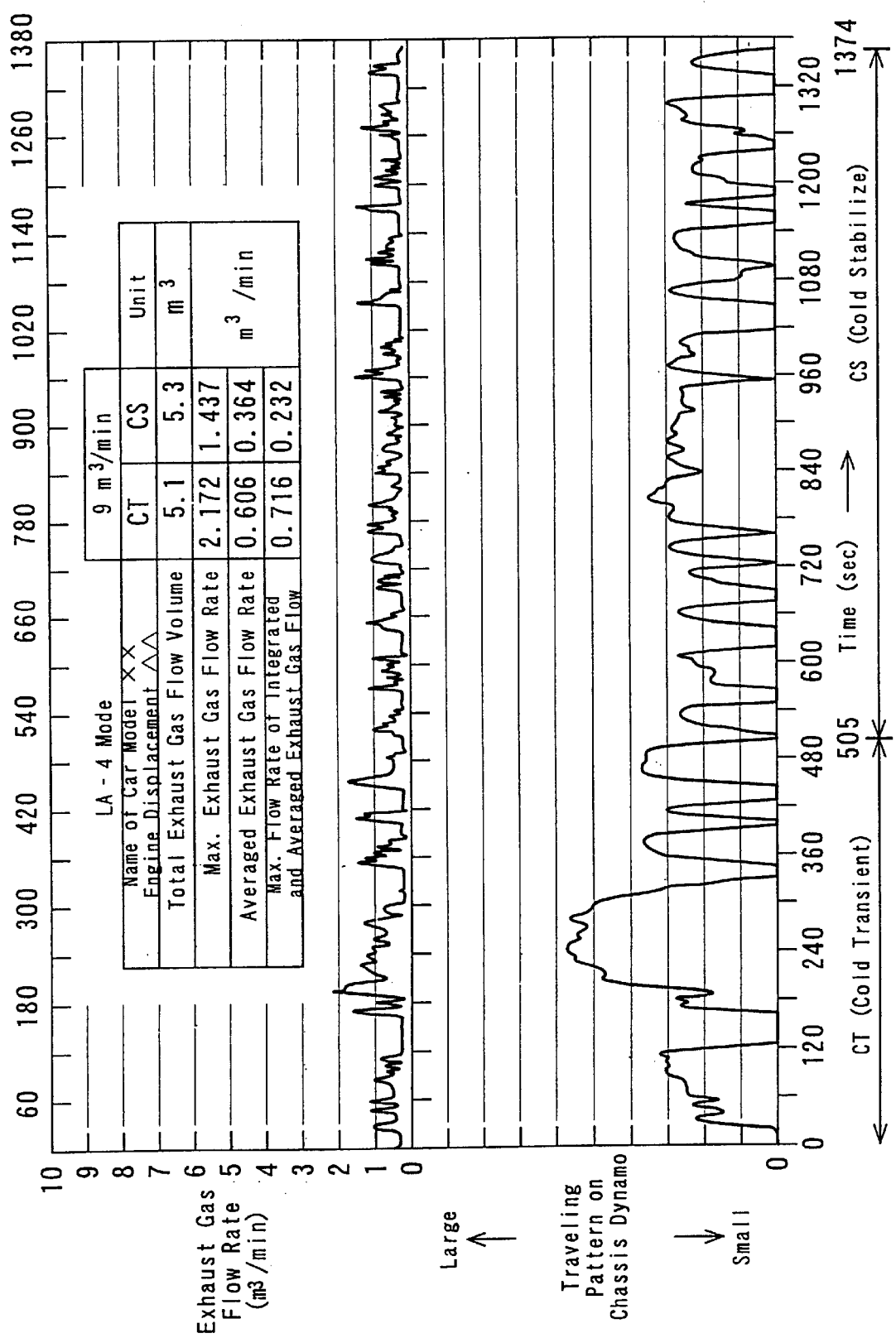
FIG. 6 is a graph showing a measurement result of exhaust gas in a cold transient (CT) phase and a cold stabilize (CS) phase (LA-4 mode), as well as a traveling pattern (i.e., car speed) on a chassis dynamo.

FIG. 6 shows the measurement result of the flow rate of exhaust gas and the detected result of the specific components therein, in the cold transient (CT) phase and the cold stabilize (CS) phase (LA-4 mode). In FIG. 6, the vertical axis indicates the time (in seconds), i.e., elapsed time from the time point of starting of the engine. In an upper part is indicated the flow rate of the exhaust gas. In a lower part thereof is indicated the traveling pattern (i.e., the car speed) on the chassis dynamo.

Figure 7:
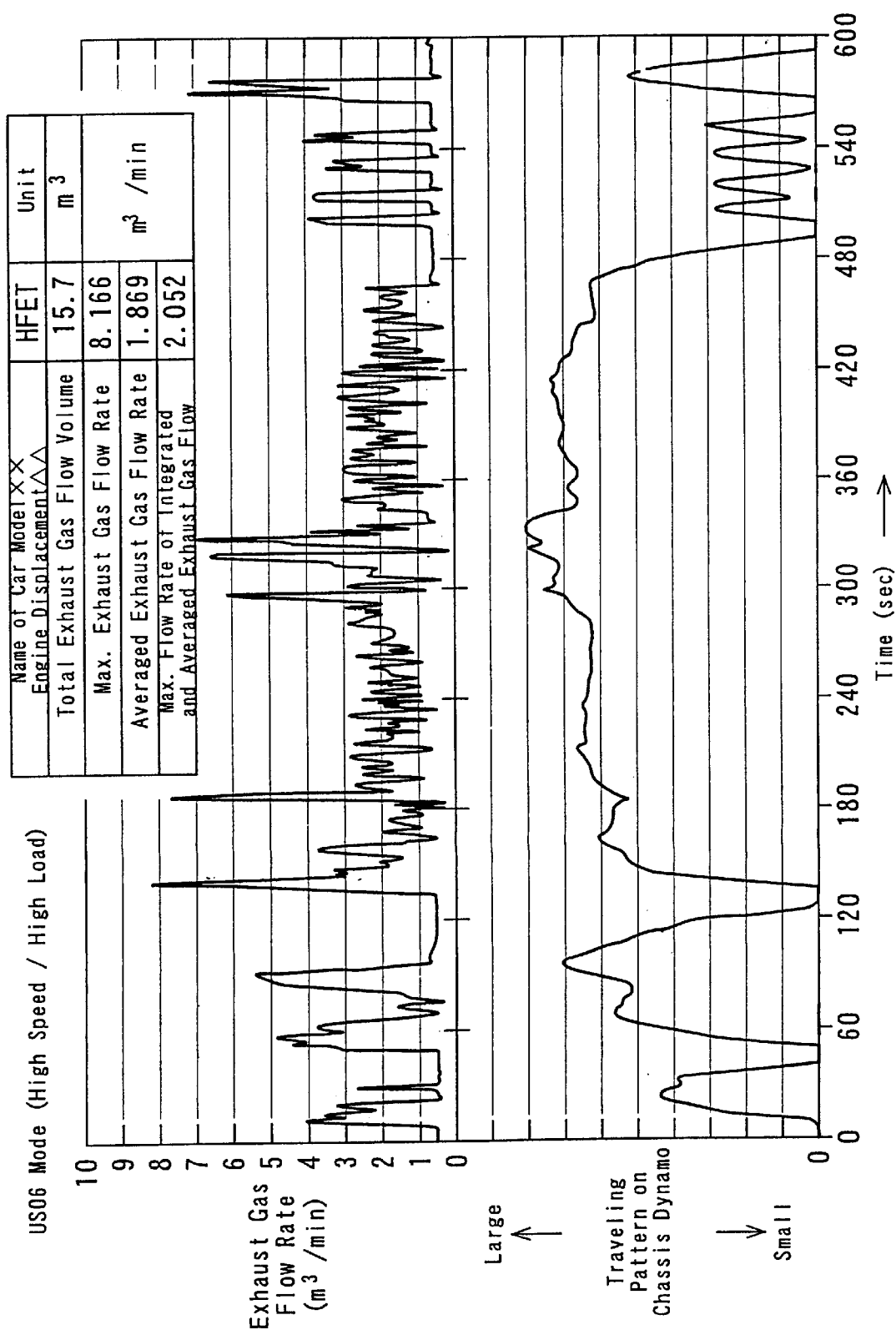
FIG. 7 is a graph showing a measurement result of exhaust gas in US06 mode (high speed/high load), as well as a traveling pattern (i.e., car speed) on a chassis dynamo.

FIG. 7 is a graph showing the measured result of the flow rate of exhaust gas and the detected result of the specific components therein, in the US06 mode (high speed/high load mode). In FIG. 7, the vertical axis also indicates the time (in seconds), and in an upper part is indicated the flow rate of the exhaust gas, while in a lower part thereof the traveling pattern (i.e., the car speed) on the chassis dynamo is indicated.

In this manner, with use of the flow rate detector mechanism 1 with the variable venturi shown in FIG. 1, it is possible to obtain the instantaneous flow rate over a short time period in sequence such as, for example, 10 msec, therefore the change in flow rate of the diluted gas can be determined correctly. Accordingly, it is possible to perform the measurement of exhaust gas and the analysis of contents thereof with higher accuracy.

Next, explanation will be given of a method according to the present invention for sampling exhaust gas, wherein the exhaust gas is diluted to be sampled in the sampling bags, corresponding to the traveling mode pattern for evaluation test and using the flow rate detector mechanism 1 with the variable venturi mentioned in the above.

TABLE 1

Relationship CVS Flow Rate v. Sampling Flow Rate

| CVS Flow Rate | Sampling Flow Rate |
|---|---|
| 0.6 m³/min (600 liter/min) | 3 liter/min |
| 1.0 m³/min (1,000 liter/min) | 5 liter/min |
| 1.8 m³/min (1,800 liter/min) | 9 liter/min |
| 2.4 m³/min (2,400 liter/min) | 12 liter/min |

The above TABLE 1 shows a relationship between the CVS flow rate (flow rate of the diluted gas) and the sampling flow rate, and FIG. 8 shows a sequences for changing the flow rate of the diluted gas in the LA-4 mode. In this embodiment, as shown in TABLE 1, the flow rate of diluted gas and the sampling flow rate are changed or altered in four (4) stages. Under the condition where the discharged amount of the exhaust gas is very small in volume, for example when traveling in idling condition or the like, the flow rate of the diluted gas is set at 0.6 m³/min (600 l/min), and the sampling flow rate (sampling flow volume into the diluted gas sampling bag) is set at 3 liter/min, this being equal to one-two-hundredth (1/200) of the flow rate of diluted gas. Under the condition where the discharged amount of the exhaust gas is small in volume, for example when traveling at a constant speed condition, the flow rate of the diluted gas is set at 1.0 m³/min (1,000l/min), and the sampling flow rate (sampling flow volume into the diluted gas sampling bag) is set at 5 liter/min, this being equal to one-two-hundredth (1/200) of the flow rate of diluted gas. Under the condition where the discharged amount of the exhaust gas is large in volume, for example when traveling in a high speed condition or accelerating/decelerating condition, the flow rate of the diluted gas is set at 1.8 m³/min (1,800 l/min), and the sampling flow rate (sampling flow volume into the diluted gas sampling bag) is set at 9 liter/min, this being equal to one-two-hundredth (1/200) of the flow rate of diluted gas. Under the condition where the discharged amount of the exhaust gas is larger still in volume, for example when traveling in a high speed condition or accelerating/decelerating condition, the flow rate of the diluted gas is set at 2.4 m$^3$/min (2,400 l/min), and the sampling flow rate (sampling flow volume into the diluted gas sampling bag) is set at 12 liter/min, this being equal to one-two-hundredth (1/200) of the flow rate of diluted gas.

In a traveling mode such as the LA-4 mode, etc., the time schedules are determined corresponding to the time periods, including idling time period, acceleration time period, traveling time period of a predetermined constant speed, and so on, as shown in FIG. 8, therefore, the sequence for changing the flow rate of the diluted gas and the sampling flow rate is prepared in advance, corresponding to the time schedule from the time point of starting the test traveling, and the controller 90 controls the flow rates in the variable venturi 1 and the sampling venturi 3 on the basis of this sequence for changing the flow rates.

Figure 9:
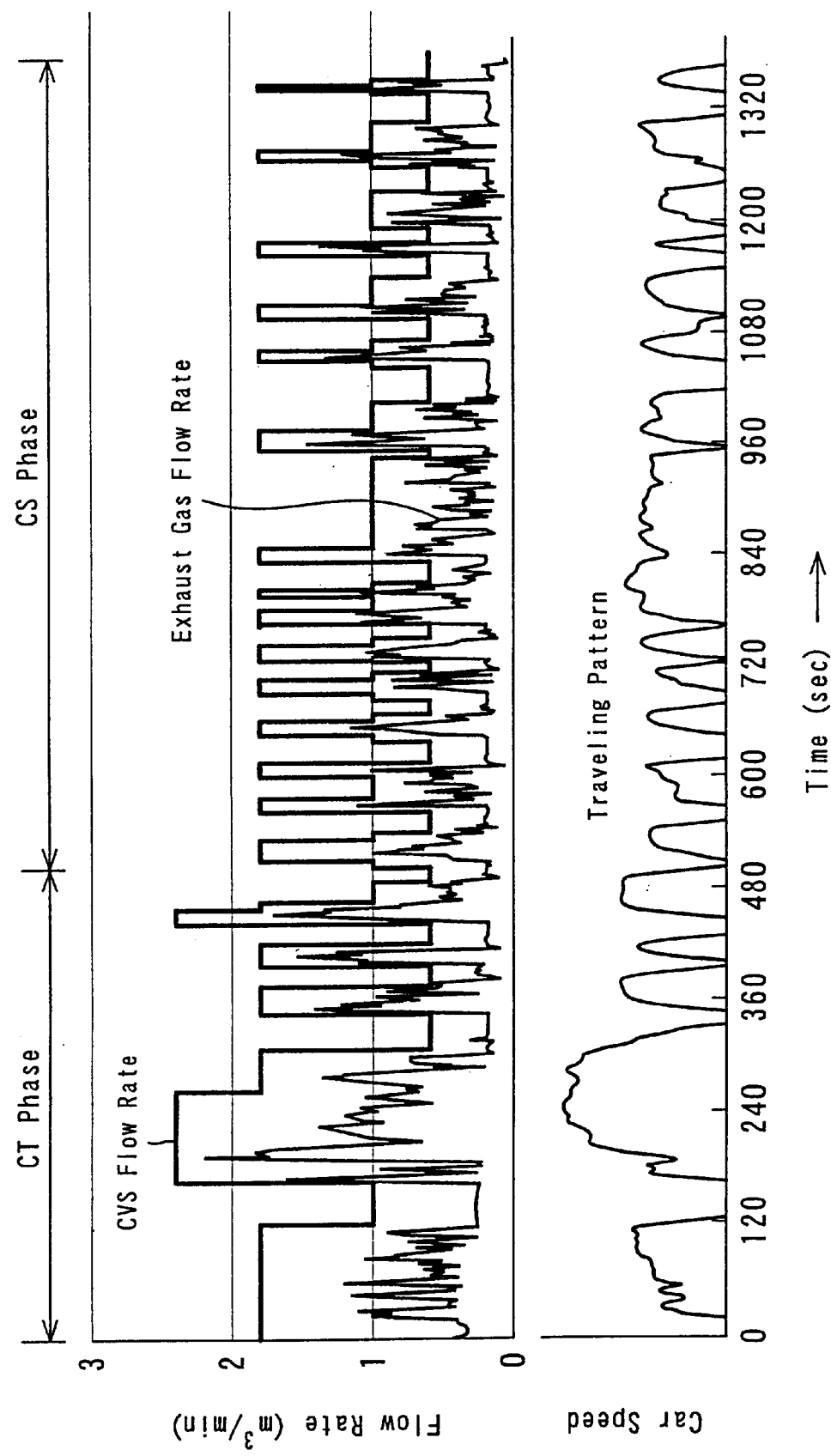
FIG. 9 is a graph showing a relationship between the exhaust gas flow rate and CVS flow rate when applying an exhaust gas sampling method according to the present invention.
Figure 10:
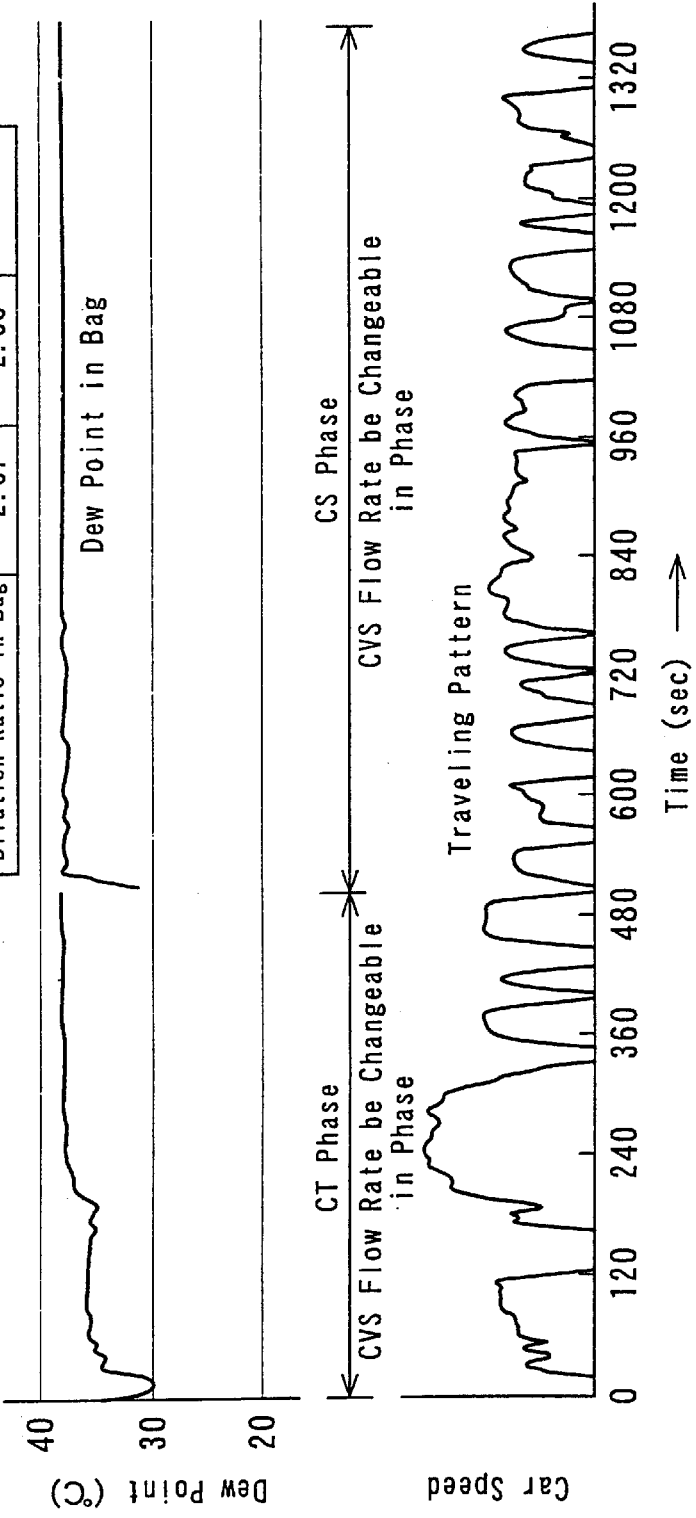
FIG. 10 is a graph showing measurement result of dew point within a sampling bag when applying the exhaust gas sampling method according to the present invention.

FIG. 9 is a graph showing the relationship between the flow rate of exhaust gas and the flow rate of CVS, in a case of applying the exhaust gas sampling method according to the present invention therein, and FIG. 10 shows the results of dew points measured in the bag in a case of applying the exhaust gas sampling method according to the present invention. As shown in FIG. 9, the CVS flow rate is altered or exchanged in four (4) stages with respect to the traveling mode (car speed), therefore, there is no case where the flow rate of the exhaust gas exceeds that of the CVS. In the LA-4 mode, the minimum dilution ratio of 1.1% can be maintained by altering the CVS flow rate in accordance with the sequence for changing thereof shown in FIG. 8. Since the CVS flow rate is changed within the phase of the measuring mode, as shown in FIG. 10, it is possible to cancel the difference between the peak of dew point in the bag and the final dew point in the bag, as well as to cause the final dew point to approach the temperature at which the bag is kept.

In short, the dew point within the sampling bags can be changed by adjusting the amount flowing through the variable critical flow venturi. The following explanation will demonstrate this empirically:

From the gas flow volumes in FIG. 5, the following equation can be derived, $$V55+V3=V51+V52$$

wherein,

V55=the amount of diluted exhaust flowing through blower 55,

V3=the amount of gas taken in by the gas sampling bags through venturi 3,

V51=the amount of exhaust gas flowing through intake 51, and

V52=the amount of air flowing through fresh air inlet 52.

V3 depends upon V55 (as shown in TABLE 1). Accordingly, V3 increases when V55 increases. It should be noted that the purpose of venturi 3 is not to control the amount of sample gas flowing into the sampling bags, but rather to smooth it.

V51 depends upon the test mode, that is the number of engine rotations per unit time (TABLE 1, for example, shows the sampling flow rate changed in four test stages). Moreover, measurements become impossible if V51 becomes greater than V55. As previously described, blower 55 is set to have a capacity larger than the maximum flow rate of the venturi 10.

The dew point of the diluted gas depends on the ratios of V51 and V52. When the proportion of V52 increases, dilution increases and causes the dew point to decrease. For example, if the test mode were changed with V55 remaining the same, then V52 would decrease if V51 were to increase. When V52 decreases (that is, the dilution ratio decreases), the dew point of the diluted gas rises and condensation forms more easily. Accurate measurements become impossible when condensation occurs. Therefore, V55 is increased in such a case so that the dilution ratio will increase when V51 increases, leading to a lowering of the dew point.

In summary then, the dew point changes within the sampling bags by adjusting V55, the amount flowing through the variable critical venturi 10.

Figure 12:
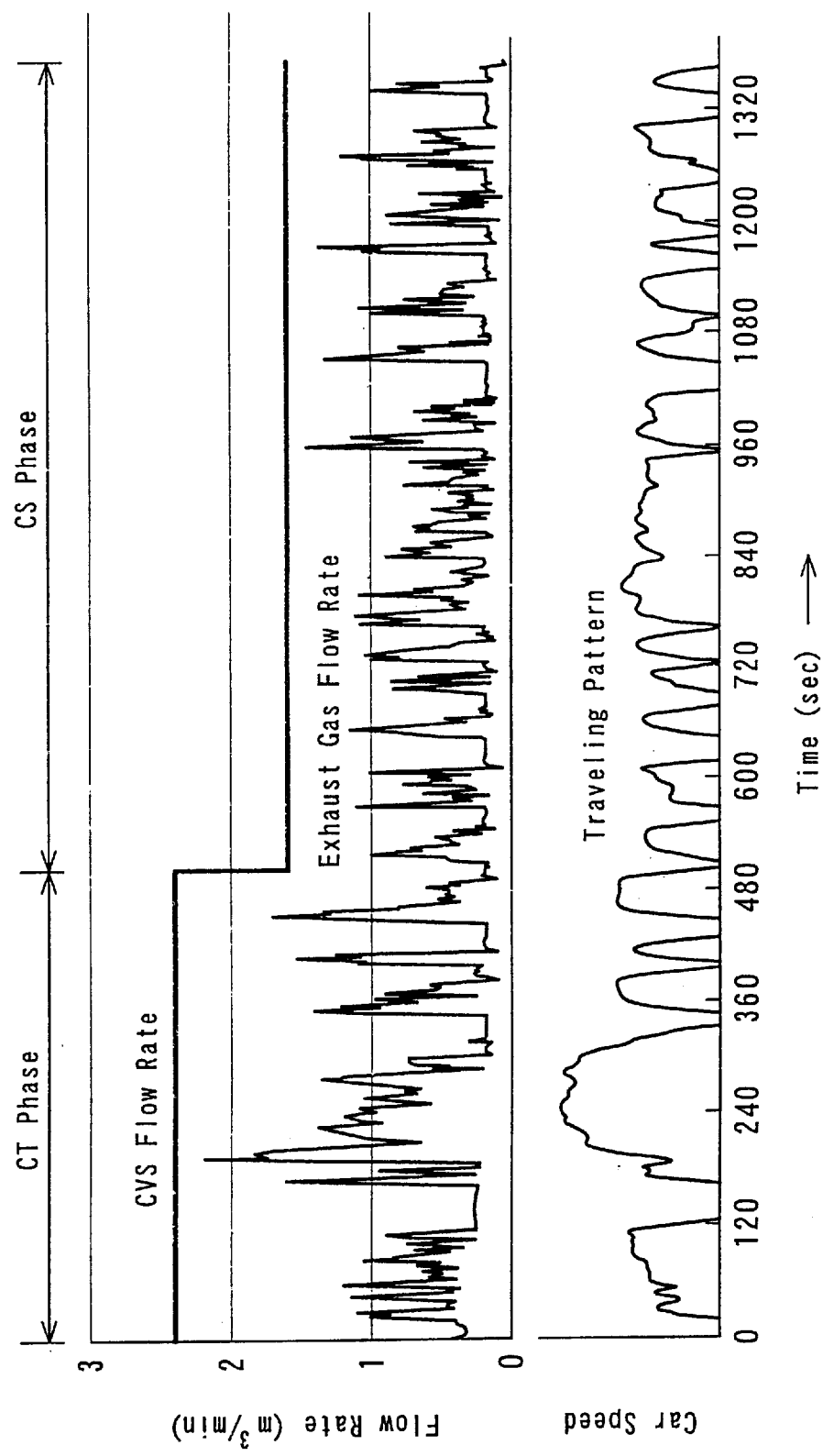
FIG. 12 is a graph from Prior Art showing a relationship between the exhaust gas flow rate and CVS flow rate in the LA-4 mode.
Figure 13:
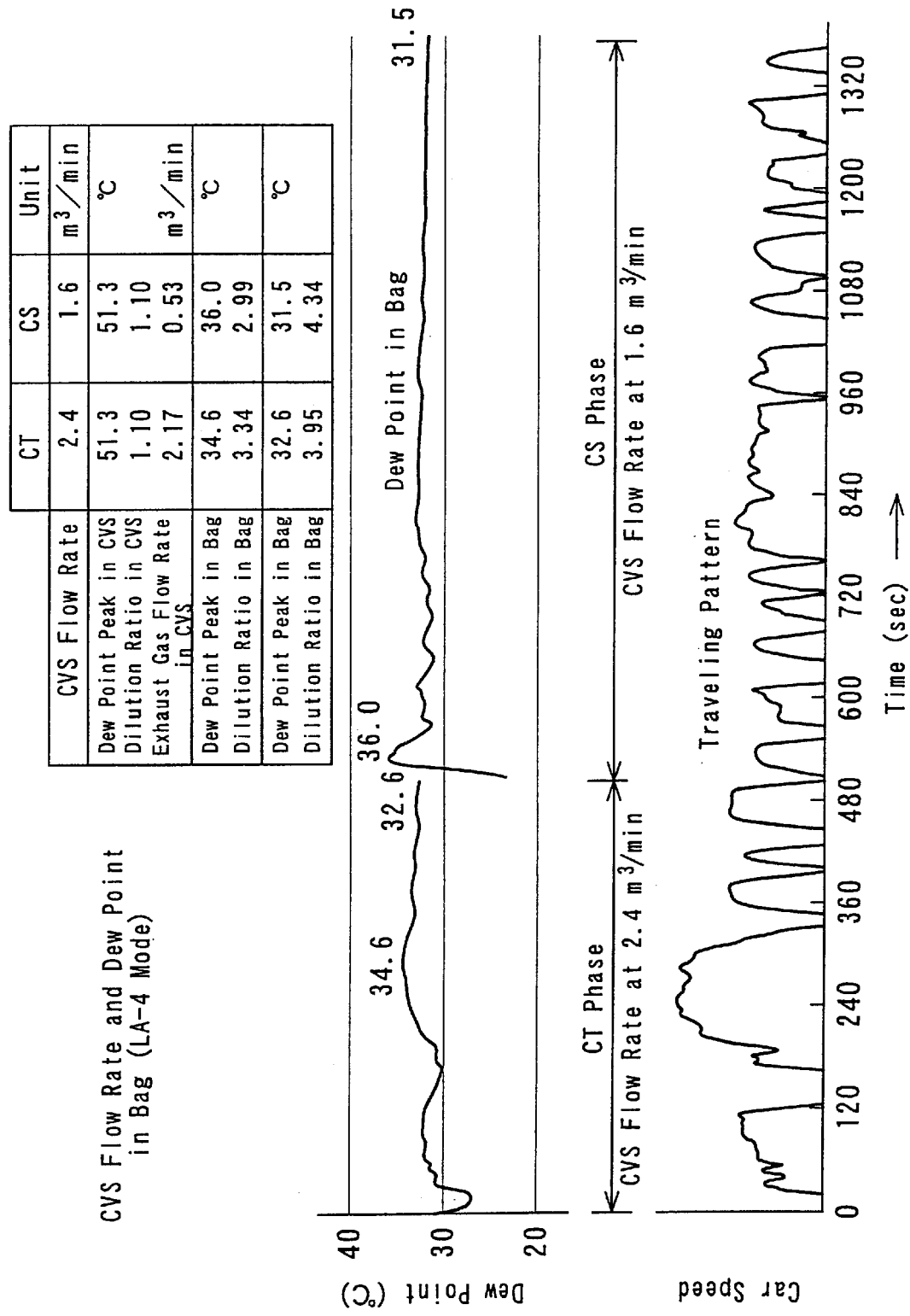
FIG. 13 is a graph from Prior Art showing dew point within the sampling bag when sampling the diluted gas with the CVS flow rate shown in FIG. 12.
Figure 14:
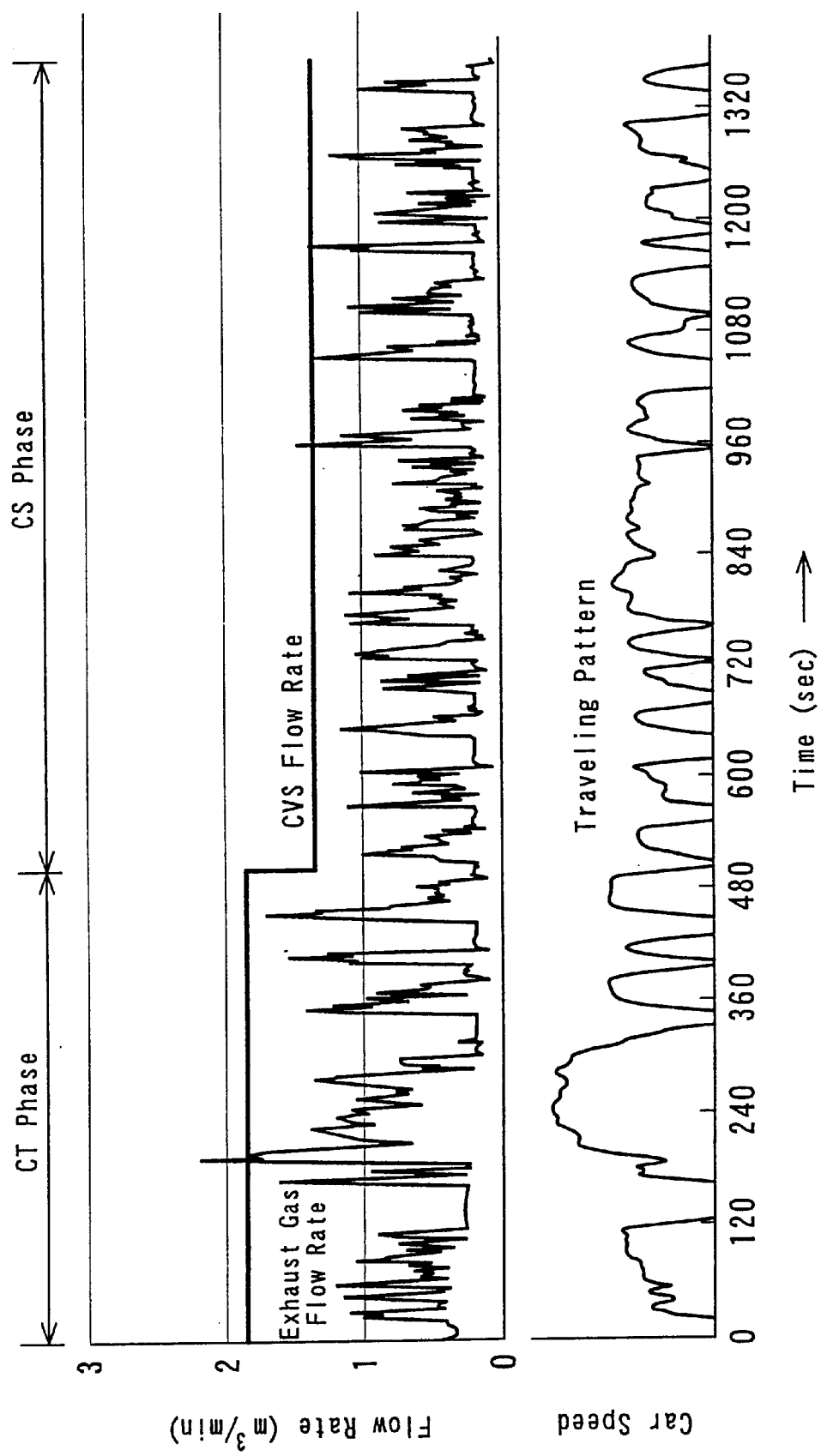
FIG. 14 is a graph from Prior Art showing a relationship between the exhaust gas flow rate and CVS flow rate in the LA-4 mode in a case where the CVS flow rate is lower than the condition shown in FIG. 12.
Figure 15:
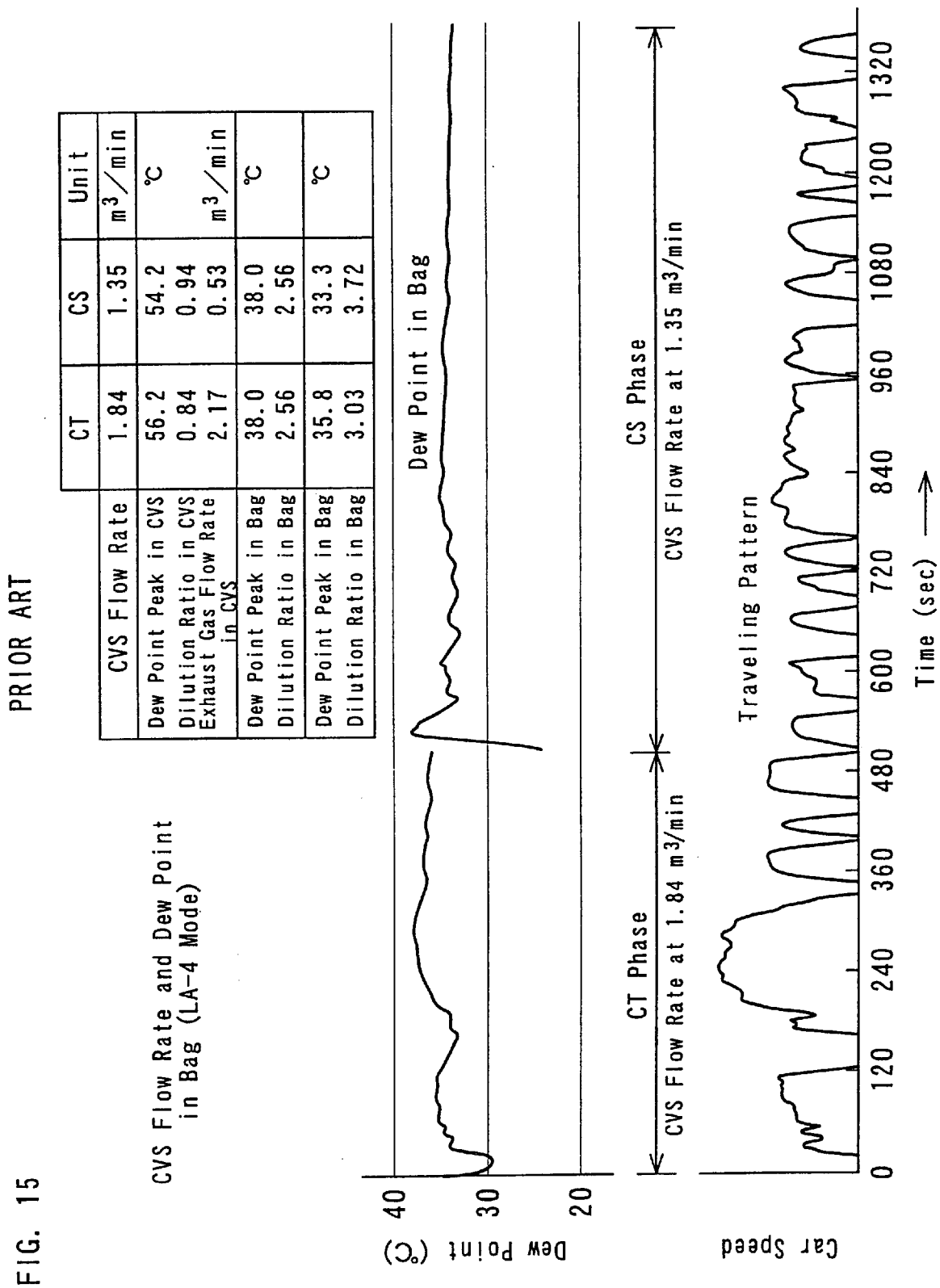
FIG. 15 is a graph from Prior Art showing dew point within the sampling bag when sampling the diluted gas with the CVS flow rate shown in FIG. 14.
Figure 16A:
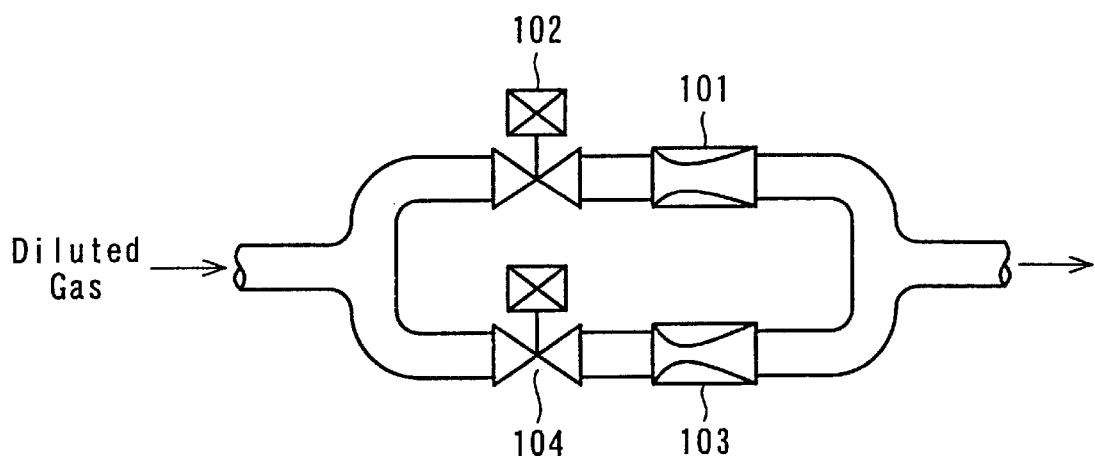
FIGS. 16(a) and (b) are explanatory views from Prior Art showing problems in a prior-art CVS apparatus when altering the flow rate of exhaust gas therewith.
Figure 16A:
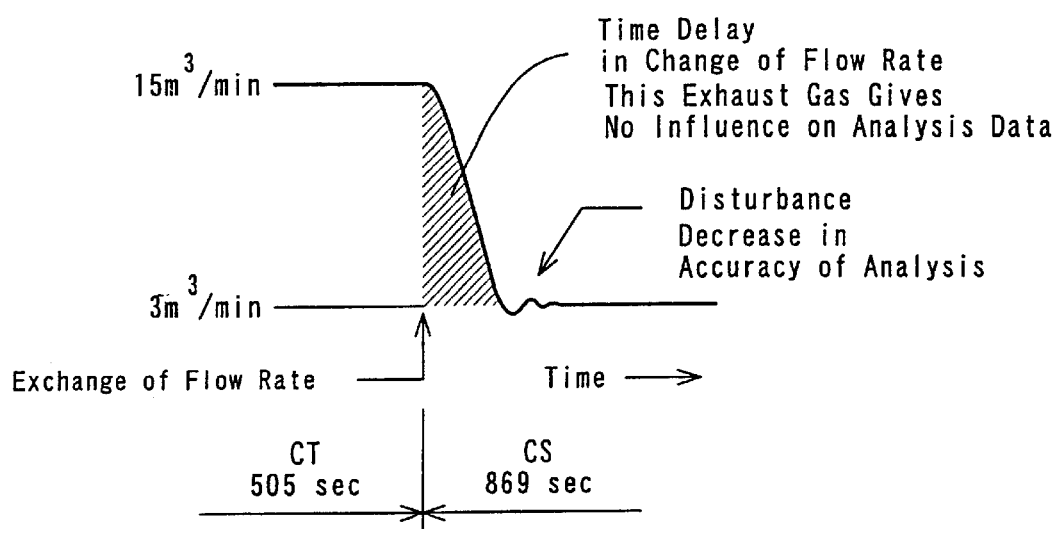

In the case of applying the exhaust gas sampling method according to the present invention, as shown in FIG. 10, the final dilution ratio in the bag is 2.57 in the CT phase, and the final dilution ratio in the bag is 2.58 in the CS phase. On the other hand, according to the conventional exhaust gas sampling method (i.e., the method of changing the flow rate of CVS for each phase) shown in FIG. 12, the final dilution ratio in the bag is 3.95 in the CT phase and the final dilution ratio in the bag is 4.34 in the CS phase, therefore it can be seen that the concentration can be rich in the diluted gas which is sampled in the sampling bag.

However, the ratio between the CVS flow rate and the sampling flow rate is always the same because the CVS flow rate being based on the phases according to the conventional exhaust gas sampling method (i.e., the CVS flow rate is changed when the phase is exchanged, but at that time the sampling bag is exchanged, therefore the ratio between the CVS flow rate and the sampling flow rate is the same). On the contrary, with the exhaust gas sampling method according to the present invention, since the CVS flow rate is changed among the phases as shown in TABLE 1, the sampling volume must be changed by the same ratio with respect to the change in the CVS flow rate.

In FIG. 5, though it is so constructed that the CVS flow rate and the sampling flow rate come to a predetermined ratio (for example, 200:1), as shown in FIG. 2, by changing the flow rate through the variable venturi 1 for setting the CVS flow rate and, at the same time, the flow rate through the sampling variable venturi 3, it is also possible to make both the CVS flow rate and the sampling flow rate variable, by combining the plurality of orifices each having a different flow rate.

Figure 11:
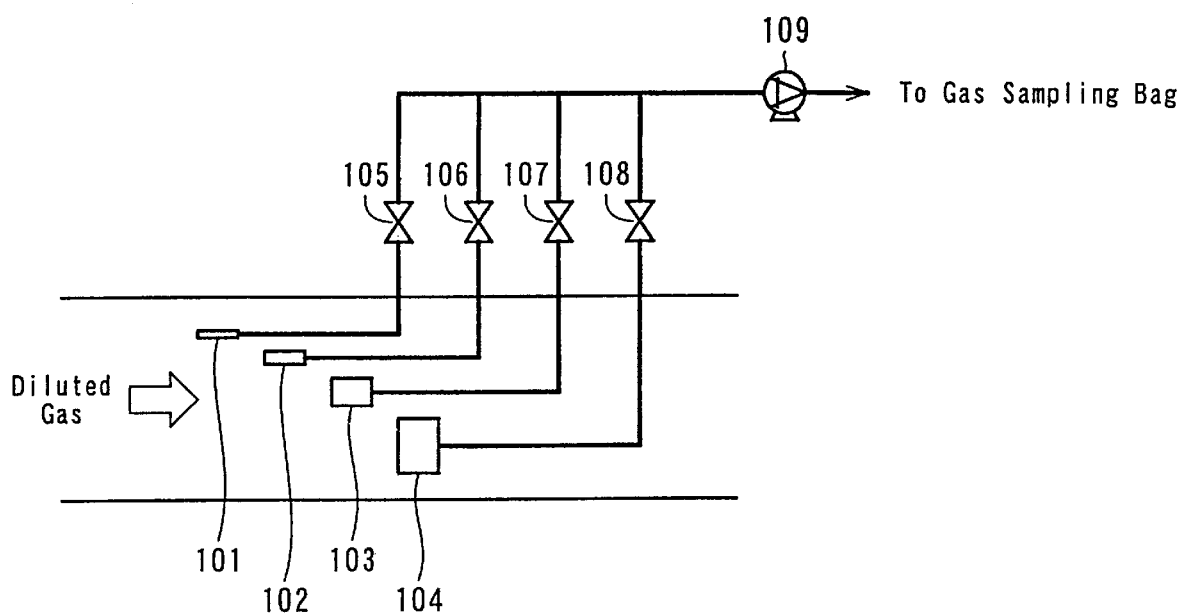
FIG. 11 is an explanatory view showing another structure of an altering mechanism of sampling gas flow, according to the present invention.

FIG. 11 is a view for explaining another structure for the sampling flow rate altering mechanism. The sampling flow rate altering mechanism shown in FIG. 11 comprises an orifice 101 of 1 liter/min in flow rate, an orifice 102 of 2 liter/min in flow rate, an orifice 103 of 4 liter/min in flow rate, and an orifice 104 of 8 liter/min in flow rate, wherein electromagnetic valves 105 to 108 are connected in series to the orifices 101 to 104, respectively. The reference numeral 109 indicates a pump for sampling the diluted gas. The selection among the orifices 101 to 104 is conducted by controlling OPEN/CLOSE of the electromagnetic valves 105 to 108. When all of the orifices 101 to 104 are used, the sampling flow rate comes to be 15 liter/min (the maximum value). This altering mechanism for the sampling flow rate is able to change by a unit of 1 liter/min within a range from 1 liter/min to 15 liter/min.

In FIG. 5, though there is disclosed the structure for altering the CVS flow rate by using the variable venturi 1 therein, it is also possible however to make the CVS flow rate variable, by exchanging the fixed venturis, each having a different flow rate, which are provided in plural in the number thereof, or by selecting the combination of the fixed venturis to be used at the same time.

In the present embodiment, there is disclosed the LA-4 mode as one example of the traveling mode, wherein the CVS flow rate and the sampling flow rate are exchanged in four (4) stages in the CT phase and the CS phase; however, the exhaust gas sampling method according to the present invention can be applied to other various traveling modes as well. However, in such instances, the CVS flow rate must be setup appropriately depending upon the displacement of the car (engine) to be measured. Further, the exchange timing of the CVS flow rate must be setup appropriately depending upon the traveling modes.

In the present embodiment, there is disclosed the construction wherein the sequence for changing the CVS flow rate and the sampling flow rate, as shown in FIG. 8, is prepared in advance, and the controller 90 controls the CVS flow rate and the sampling flow rate on the basis of the sequence for changing. However, it is also possible to construct it so that information designating the sampling flow rate is outputted from the automatic engine controller which controls the operation of the automobile on the chassis dynamo, so as to control the CVS flow rate and the sampling flow rate on the basis thereof. Further, supplying the operation information relating to the car speed, the acceleration/declaration, etc., from the chassis dynamo to the controller 90, the controller 90 can change the CVS flow rate and the sampling flow rate on the basis thereof.

As is fully explained in the above, according to the present invention, the flow rate detector mechanism using the variable venturi therein, comprises: a variable flow rate generator, comprising: a core; and a variable venturi; wherein a throat (flow passage) cross-sectional area defined between the core and the venturi is able to be changed by shifting relative positions of the core and the venturi in a direction of axes thereof, and further comprising a flow rate calculation processing portion for calculating a flow rate based on the relative positions in the direction of the axes thereof and for outputting the calculated flow rate, thereby enabling continuous change of the constant flow rate, without any disturbance in the flow rate value occurring when the flow rate is changed. Further, the flow rate detector mechanism using the variable venturi, according to the present invention, is able to output the output even during the flow rate being altered or exchanged. Therefore, by using the flow rate detector mechanism with the variable venturi according to the present invention, no error is contained in the result of analysis even when the diluted gas is changed in flow rate depending upon the test modes, thereby obtaining the result of analysis with high accuracy.

Also, as is fully explained in the above, with the exhaust gas sampling method according to the present invention, since the CVS flow rate is changed within the range of the phases of measure modes, it is possible to make small the difference between the peak of the dew point in the bag and the final dew point in the bag, as to cause the final dew point to approach the temperature at which the bag is kept. Therefore, the dilution ratio of the final dew point in to bag can be decreased, so as to improve the accuracy of analysis.

What is claimed is:

1. An exhaust gas sampling method for analyzing exhaust gas of an automobile, using a flow rate detector mechanism using a variable venturi therein, comprising the following steps:

diluting the exhaust gas from the automobile with fresh air from outside;

sampling a portion of the diluted exhaust gas into a sampling bag at a certain ratio; and analyzing the diluted exhaust gas being sampled, wherein a flow rate through said flow rate detector mechanism is changed in a phase of mode for measurement, so that at least a final dew point in the sampling bag approaches a predetermined temperature within a predetermined range of temperature.

2. The exhaust gas sampling method as defined in claim 1, wherein the flow rate through said flow rate detector mechanism is changed in the phase of mode for measurement, so that the dew points in the sampling bag are averaged.

3. The exhaust gas sampling method as defined in claim 1, wherein the flow rate through said flow rate detector mechanism is changed in the phase of mode for measurement, so that at least the flow rate through said flow rate detector mechanism does not exceed the flow rate of the exhaust gas during measurement.

4. The exhaust gas sampling method as defined in claim 1, wherein the flow rate of the sampling is changed depending upon the change in the flow rate through said flow rate detector mechanism.

\* \* \* \* \*